United States Patent [19]

Sawa et al.

[11] Patent Number: 4,523,597
[45] Date of Patent: Jun. 18, 1985

[54] APPARATUS AND METHOD FOR MEASURING THE INTRAOCULAR PRESSURE OF AN EYEBALL AND AUXILIARY DEVICE FOR USING THEREWITH

[75] Inventors: Seiji Sawa, Sakai; Nobuyuki Kita, Osaka, both of Japan

[73] Assignee: Minolta Camera Kabushiki Kaisha, Osaka, Japan

[21] Appl. No.: 566,485

[22] Filed: Dec. 29, 1983

[30] Foreign Application Priority Data

| Dec. 29, 1982 | [JP] | Japan | 57-228557 |
| Apr. 8, 1983 | [JP] | Japan | 58-62778 |
| Nov. 21, 1983 | [JP] | Japan | 58-219767 |
| Nov. 22, 1983 | [JP] | Japan | 58-220066 |
| Dec. 22, 1983 | [JP] | Japan | 58-243575 |

[51] Int. Cl.³ .............................................. A61B 3/16
[52] U.S. Cl. .................................................. 128/652
[58] Field of Search .................... 128/645, 652; 73/81

[56] References Cited

U.S. PATENT DOCUMENTS

| 3,070,997 | 1/1963 | Papritz et al. | |
| 3,756,073 | 9/1973 | Lavallee et al. | |
| 3,977,237 | 8/1976 | Tesi | 128/652 |
| 3,992,926 | 11/1976 | Berryhill | 128/652 |
| 4,164,863 | 8/1979 | Raysdale | 128/652 |
| 4,192,317 | 3/1980 | Munnerlyn et al. | |
| 4,209,021 | 6/1980 | Warming | 128/652 |
| 4,213,464 | 7/1980 | Katz et al. | 128/652 X |

FOREIGN PATENT DOCUMENTS 1360603  7/1974  United Kingdom .
2091441  7/1982  United Kingdom .

Primary Examiner—Edward M. Coven
Attorney, Agent, or Firm—Joseph W. Price

[57] ABSTRACT

The apparatus and method for measuring the intraocular pressure of an eyeball is constructed so that the image of the fluorescent ring around the flattened surface of the eyeball is formed to measure the area of the flattened surface, and that the intraocular pressure of the eyeball is calculated in accordance with the pressure against the eyeball and the area of the flattened surface corresponding thereto.

39 Claims, 51 Drawing Figures

FIG.1 PRIOR ART
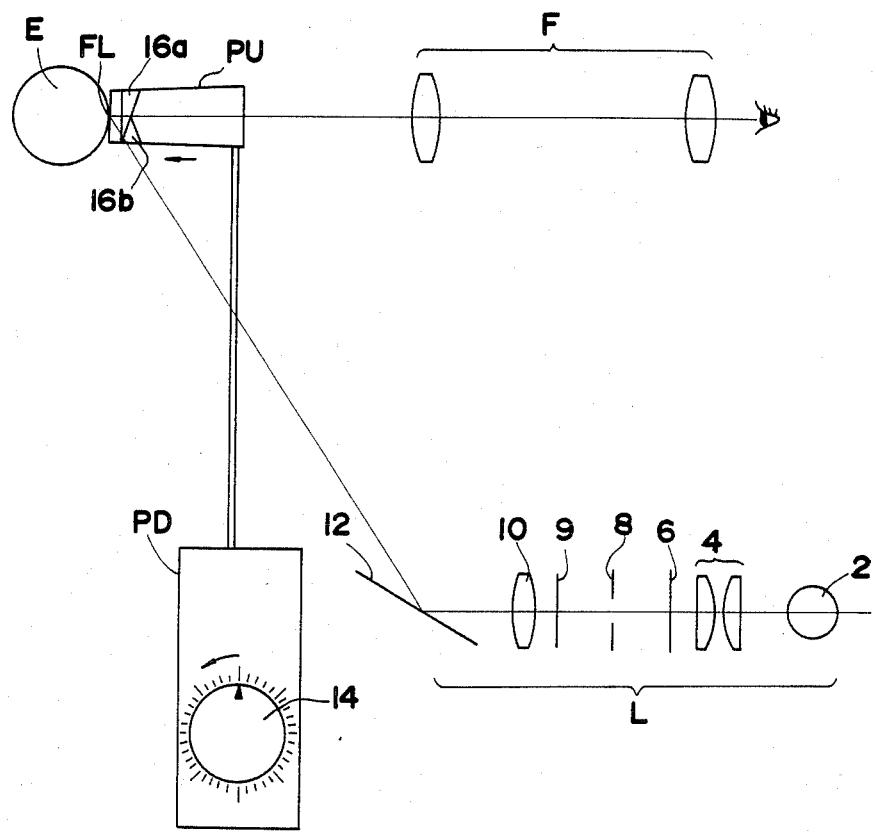
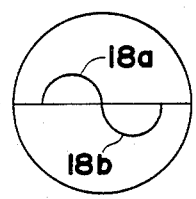
FIG.2a
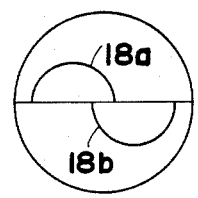
FIG.2b
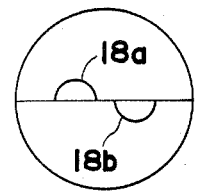
FIG.2c
PRIOR ART

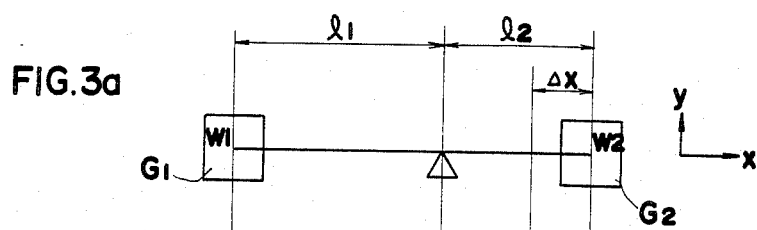
FIG.3a
FIG.3b
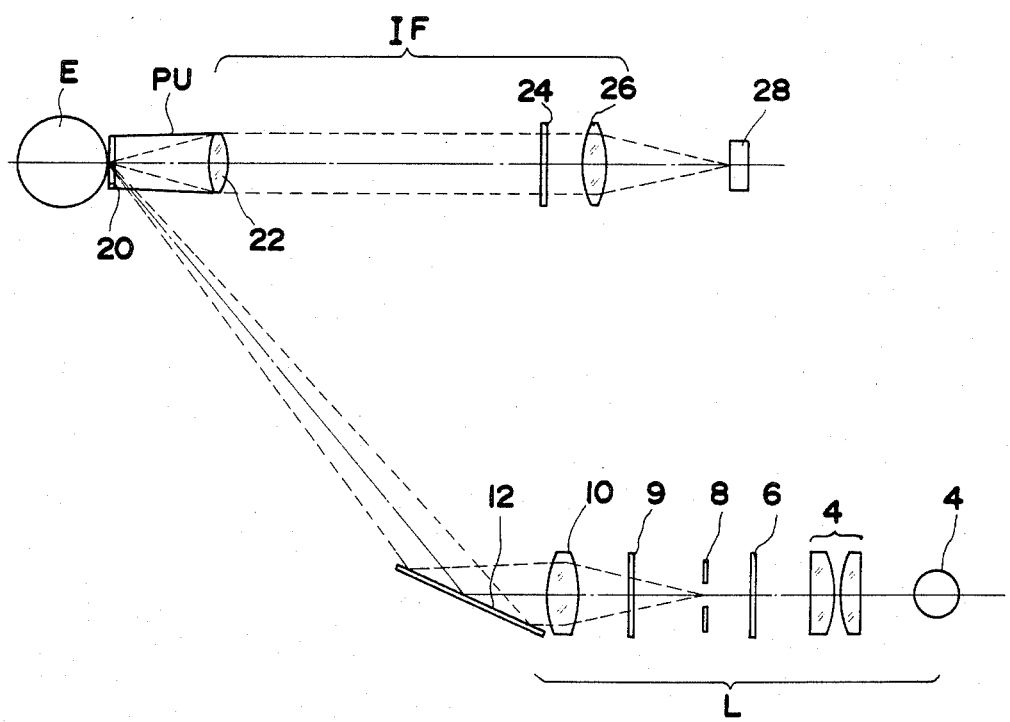
FIG.4

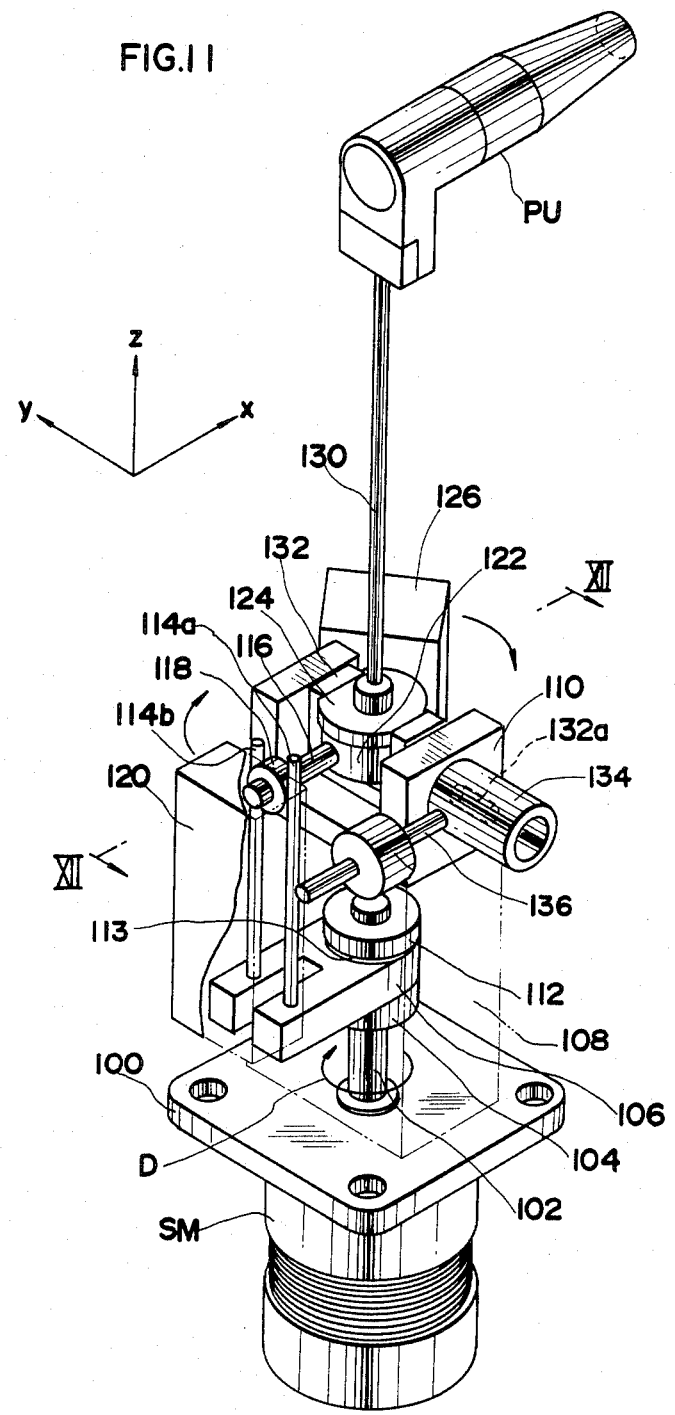

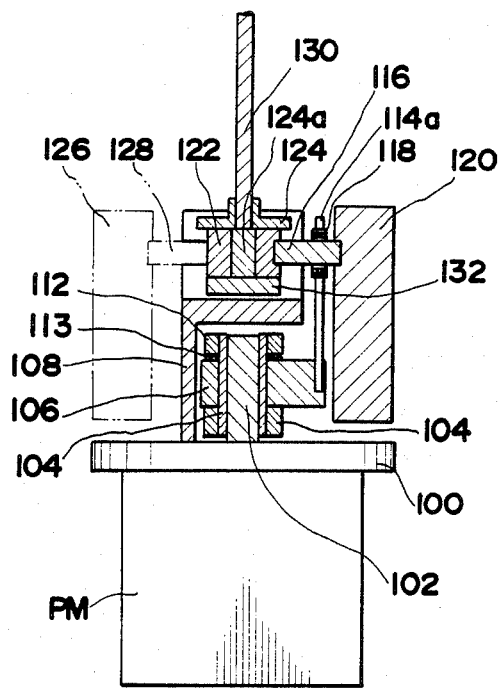
FIG.12
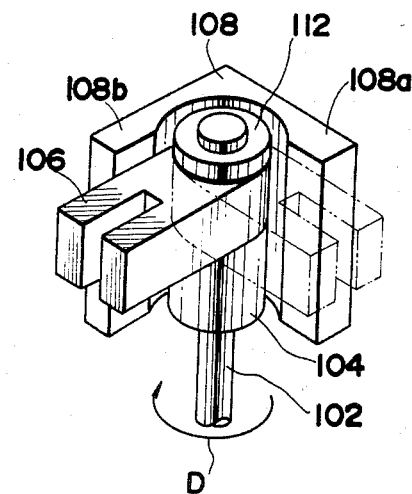
FIG.13
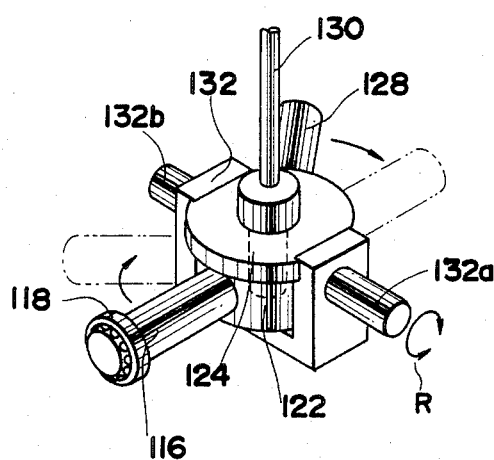
FIG.14
FIG.15

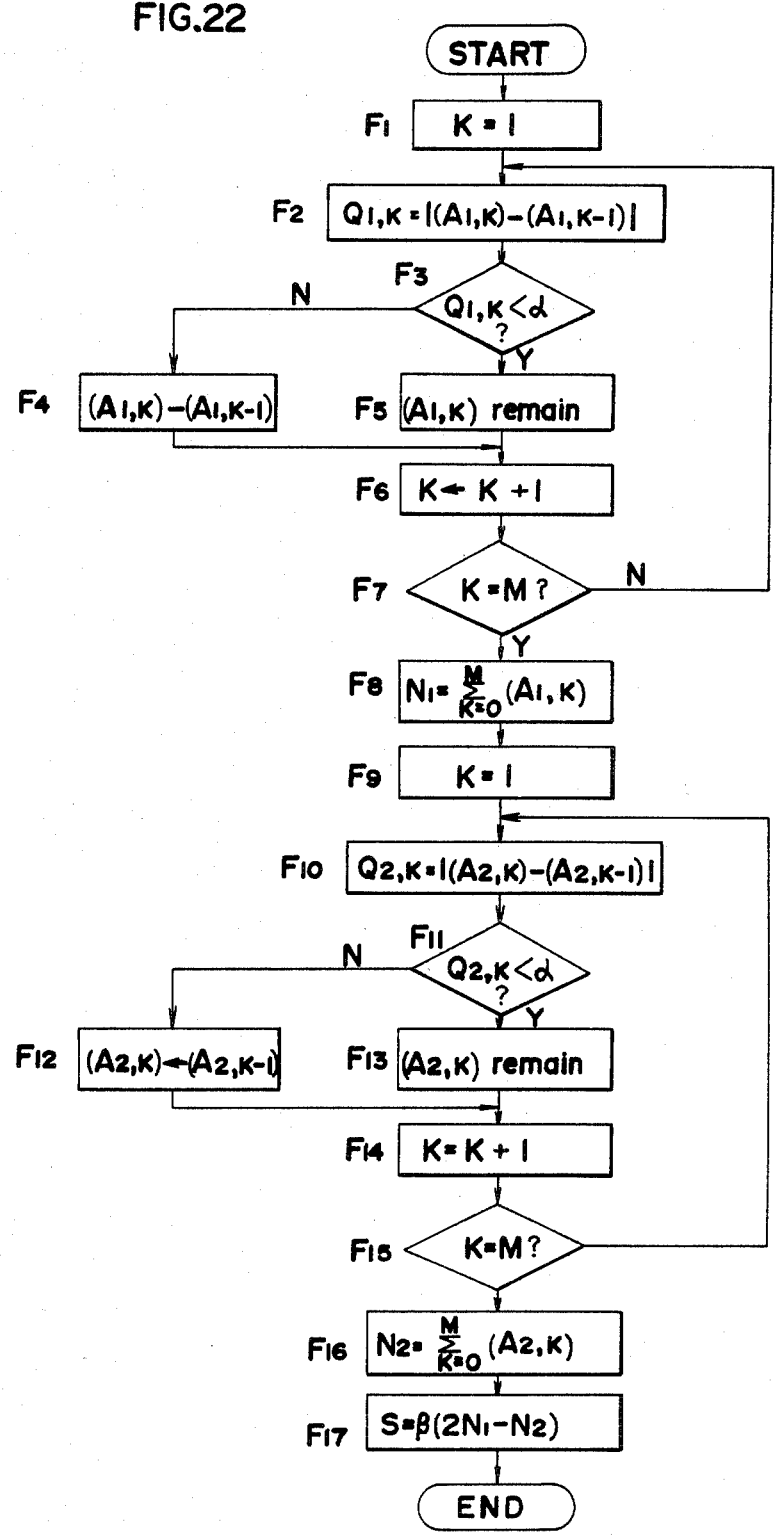

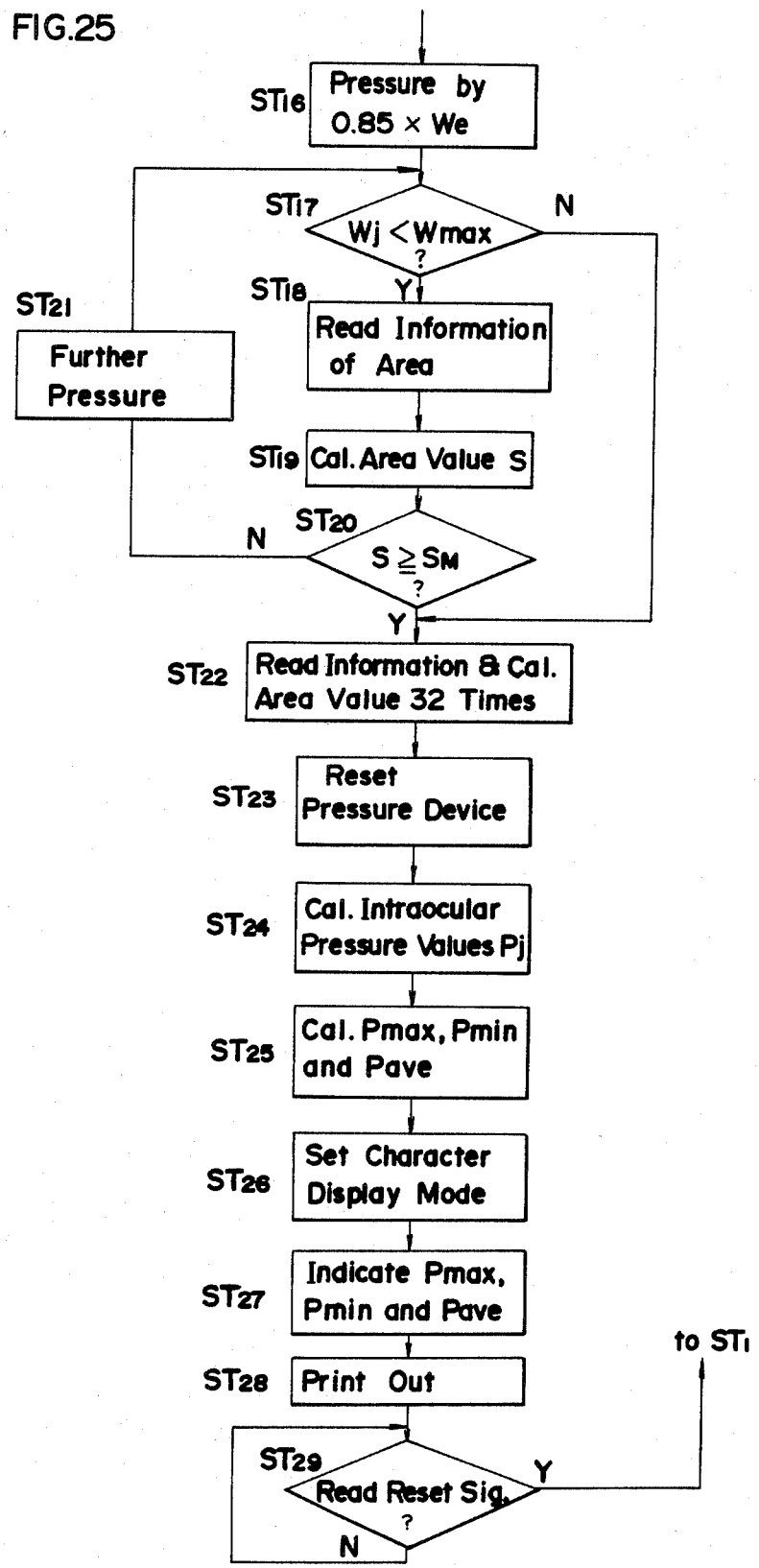

APPARATUS AND METHOD FOR MEASURING THE INTRAOCULAR PRESSURE OF AN EYEBALL AND AUXILARY DEVICE FOR USING THEREWITH

BACKGROUND OF THE INVENTION

1. Field of the Invention

This invention relates to an apparatus and method for measuring the intraocular pressure of an eye, to an applanation device using therefor, and to an auxiliary device using therewith.

2. Description of the Prior Art

Measurement of the intraocular pressure of an eye is effective in the prevention against glaucoma, for the early discovery thereof, and for the diagnosis thereof. Furthermore, such measurement is utilized for monitoring the progress of the eye which has been treated or operated for glaucoma. The possibility that glaucoma causes a loss of sight is as realistic as the possibility that diabetic retinopathy (retinopathia diabetica) causes it.

Therefore, in a plurality of ophalmological examinations, the measurement of the intraocular pressure is most routinely performed much the same as the photographing of the fundus of an eye is performed.

The history of intraocular pressure determination had its beginnings in palpation but the Goldmann tonometer as taught by U.S. Pat. No. 3,070,997 solved the problem of ocular rigidity and has since been used by ophthalmologists as the most reliable device for measuring the intraocular or tonometric pressure.

As illustrated in FIG. 1, the Goldmann tonometer has a lighting system (L) consisting of a tungsten light source (2), a consenser lens (4), and infrared-near infrared cut filter (6), an aperture (8) a blue filter (9), a projection lens (10) and a mirror (12) for projecting a blue light on a flattened plane of the eye. An applanation pickup (PU) for flattening the frontal surface of the eyeball (E) to be examined, an applanation drum (PD) equipped with a manual dial (14) for adjusting the pressure with which said applanation pickup (PU) pushes the eyeball (E), and a finder (F) through which the examiner observes the flattened surface of the eye are provided. The front surface (which is brought into contact with the eyeball) of the pickup (PU) is a transparent flat surface which is provided with two microprisms (16a), (16b) in close contact therewith. In measuring the intraocular pressure, fluorescein (a fluorescent substance) is instilled into the examined eye and, then, the manual dial (14) of the applanation drum (PD) is manipulated so that the eyeball (E) will be gradually pressed by the pickup (PU). The lighting system (L) illuminates the front surface of the pickup (PU) with blue light alone so that the image of the aperture 8 is formed on this surface. As the eyeball (E) is gradually pressed by the applanation pickup (PU) with increasing the pressure, the front surface of the eyeball is progressively flattened and consequently the fluorescein is pooled around the flattened area. The dispersion spectrum peak of fluorescein (FL) and the excited spectrum peak lie in the neighborhood of 490 mm and 520 mm, respectively, and as the blue light excites the fluorescein (FL), a green fluorescent ring is formed around the flattened area. This area enclosed by the fluorescent ring shows the size of the flattened surface.

In the Goldmann tonometer, when this fluorescein ring is observed through finder (F), it appears like FIGS. 2(a), (b) (c) due to the effect of prisms (16a), (16b). It is so arranged that when the diameter of this fluorescein ring is just 3.06 mm, the two semicircles (18a), (18b) are brought into contact with each other as illustrated in FIGS. 2(a) (b) (c). When the diameter is more than 3.06 mm and less than 3.06 mm, the semicircular images are as illustrated in FIGS. 2(b) and (c), respectively. This diameter of 3.06 mm was set because the ocular rigidity of the eyeball can be disregarded. Therefore, as the examiner manipulates the manual dial (14) of the applanation drum (PD) while observing the fluorescein ring image (18a), (18b) and stops increasing of the pressure at the moment when said two semicircles are just brought into contact with each other as shown in FIG. 2(a), the rotational position of the manual dial (14) can be used to read the applanation pressure value W (g). Then, the intraocular pressure P (mmHg) can be determined by multiplying this W (g) value by 10.

This principle is based on the following rationale. Assuming that the shape of the flattened area is a circle with a diameter of 1 (mm) and an area of S (cm²) the intraocular pressure P can be expressed by the following equation.

$$P = \frac{760}{1033.6} \times \frac{W}{S} \tag{1}$$

Since $$S = \left(\frac{1}{2} l \times \frac{1}{10}\right)^2 \times \pi,$$

$$P = \frac{760}{1033.6} \times \frac{W}{\left(\frac{1}{2} l \times \frac{1}{10}\right)^2 \times \pi} \tag{2}$$

While $l = 3.06$ mm, $$P \approx 10 W \tag{3}$$

The applanation pickup (PU) is supported by a support bar which is supported at a fulcrum in a predetermined position, and a weight is mounted movably along the support bar on the opposite side of the fulcrum of the bar with respect to the applanation pickup. By manipulating the dial by hand, the weight is moved along the support bar to vary the pressure of the applanation of eyeball by the applanation pickup at the other end of the support bar.

The fundamental principle of this applanation device is now explained with reference to FIGS. 3(a), (b).

Let it be assumed as shown in the side-elevation view of FIG. 3 (a), the weight $G_1$ weighing $W_1$ at distance $l_1$ from the fulcrum is in balance with the weight $G_2$ weighing $W_2$ at distance $l_2$ from the fulcrum. In this condition, the relation holds.

$$W_1 \cdot l_1 = W_2 \cdot l_2 \tag{4}$$

This balance is upset when, as in FIG. 3 (b), the weight $G_2$ is displaced by distance $\Delta x$ along direction x toward the fulcrum, with the result that a counter-clockwise rotation moment M is generated. This rotation moment is expressed as follows.

$$M = W_1 \cdot l_1 - W_2 \cdot (l_2 - \Delta x) \tag{5}$$

In the Goldmann tonometer, the rotation moment is varied by shifting the weight linearly so as to vary the applanation pressure to the eyeball.

However, this and analogous tonometers have the various disadvantages mentioned below. First, as will be apparent from the above explanation of the basic principle, the shape of the flattened plane is assumed to be circular. However, the precision of measurement is low when the shape is not circular as a measured eye has with astigmatism. As a procedure for correcting for this disadvantage, the applanation pickup (PU) is rotated by a predetermined angle for measuring an eye which has severe astigmatism. However, since the directionality of astigmatism differs from one subject to another, the method does not ensure an accurate measurement of intraocular pressure in all cases and complicates the measuring procedure. Moreover, unless the position of the pickup (PU) relative to the eyeball (E) are precisely controlled so that the boundary between the two prisms (16a) (16b) will pass through the center of the applanation area, the true diameter of the flattened plane cannot be measured. It causes the deterioration of the accuracy of measurement. Therefore, the position of the pickup (PU) relative to the eyeball (E) must be controlled with accuracy and this adds to complexity of the measuring procedure. In addition, owing to the bleeding of instilled fluorescein into the flattened plane, the two semicircular images (18a) (18b) observed are fairly blurred. Moreover, the diameter of the flattened plane fluctuates constantly owing to the beating of the heart. Therefore, not only a high degree of skill is required for detection of the moment at which the two semicircular images come into contact as shown in FIG. 2 (a) but also individual differences are inevitable so that the precision of measurement is adversely affected. Moreover, in the Goldmann tonometer, the intraocular pressure is measured only when the diameter of the fluorescein ring is 3.06 mm. Therefore, when the two semicircular images are shifted from the condition of contact to the condition depicted in FIG. 3 (b) or (c), the diameter of the flattened plane cannot be ascertained, with the result that the fluctuations of intraocular pressure due to the beating of the subject's heart, that is the maximum, minimum, and mean intraocular pressure, for instance, cannot be determined.

Furthermore, if it is attempted to achieve an automatic applanation with the applanation mechanism of Goldmann, the following problems are encountered. In order to vary the applanation pressure with high accuracy and control, a stepping motor may be employed. Actually, however, since the stopping motor is a device adapted to produce a rotational motion, there must be provided a mechanism for converting the rotational motion of the stepping motor to a linear motion of the weight but such a mechanism requires a complicated construction. Thus, the applanation mechanism of Goldmann tonometer is not suited to an automatic operation using a stepping motor.

Furthermore, it should be necessary to instill the fluorescein liquid into the examined eye, prior to starting the measuring operation. The following methods are applied therefor.

(1) Preserve a portion of a glass rod in the fluorescein liquid, and bring it into contact with the examined eye.

(2) Absorb the fluorescein liquid in a syringe, and instill it into the examined eye.

(3) Bring the fluorescein paper into contact with the examined eye to dissolve the fluorescein liquid, contained in the paper, by the lacrimal fluid.

However, such methods cause complexity of the preparing procedure prior to the measuring procedure. And, the delicate control of the amount of the fluorescein liquid to be instilled is rendered difficult by using such methods. Therefore, the fluorescein liquid would be instilled over an indispensable amount for measuring, and it causes dicomfort to the examined person.

SUMMARY OF THE INVENTION

This invention has been accomplished for overcoming the above-mentioned disadvantages of the Goldmann tonometer and has as its object to provide a tonometer with which the intraocular pressure can be measured expediently and with high accuracy even when said fluorescein ring is not circular, without requiring a high degree of skill on the part of the examiner and irrespective of who performs the measurement.

It is another object of this invention to provide a tonometer which is capable of measuring the changes of intraocular pressure due to the beating of the heart, i.e. the maximum, minimum and mean intraocular pressures, which could not be measured by the prior art tonometric device.

It is still another object of this invention to provide a tonometer which is capable of performing an exact and automatic measurement of intraocular pressure without demanding skill and experience on the part of the examiner.

It is a further object of this invention to provide an applanation device with the eyeball can be flattened with accuracy using a stepping motor whose rotation can be precisely controlled, the device being simple in construction.

It is a further object of this invention to provide a method and an apparatus capable of rapidly measuring the intraocular pressure of an eye.

It is a further object of this invention to provide a device effectve for decreasing the loss of wasteful fluorescein liquid.

BRIEF DESCRIPTION OF THE DRAWINGS

FIG. 1 is a schematic view outlining a prior art device;

FIGS. 2(a), (b) and (c) show the views through the finder of the prior art device;

FIGS. 3(a) and (b) are schematic diagrams illustrating the principle of applanation in the prior art device;

FIG. 4 is a simplified view showing the optical system of the tonometer as an embodiment of this invention;

FIG. 11 is a perspective view showing the applanation device of the second embodiment;

FIG. 12 is a longitudinal section view taken along the line XII—XII of FIG. 11;

FIG. 13 is a perspective view showing the stopper in the second embodiment;

FIG. 14 is a perspective view showing the main part of the applanation device in the second embodiment;

FIG. 15 is a longitudinal section view of FIG. 14;

FIG. 22 is a flow chart showing a program for calculating the area in the microprocessor of this embodiment;

FIG. 24 and FIG. 25 each is a flow chart showing the control state of the corresponding device by the microprocessor;

DETAILED DESCRIPTION OF THE PREFERRED EMBODIMENTS

Figure 5:
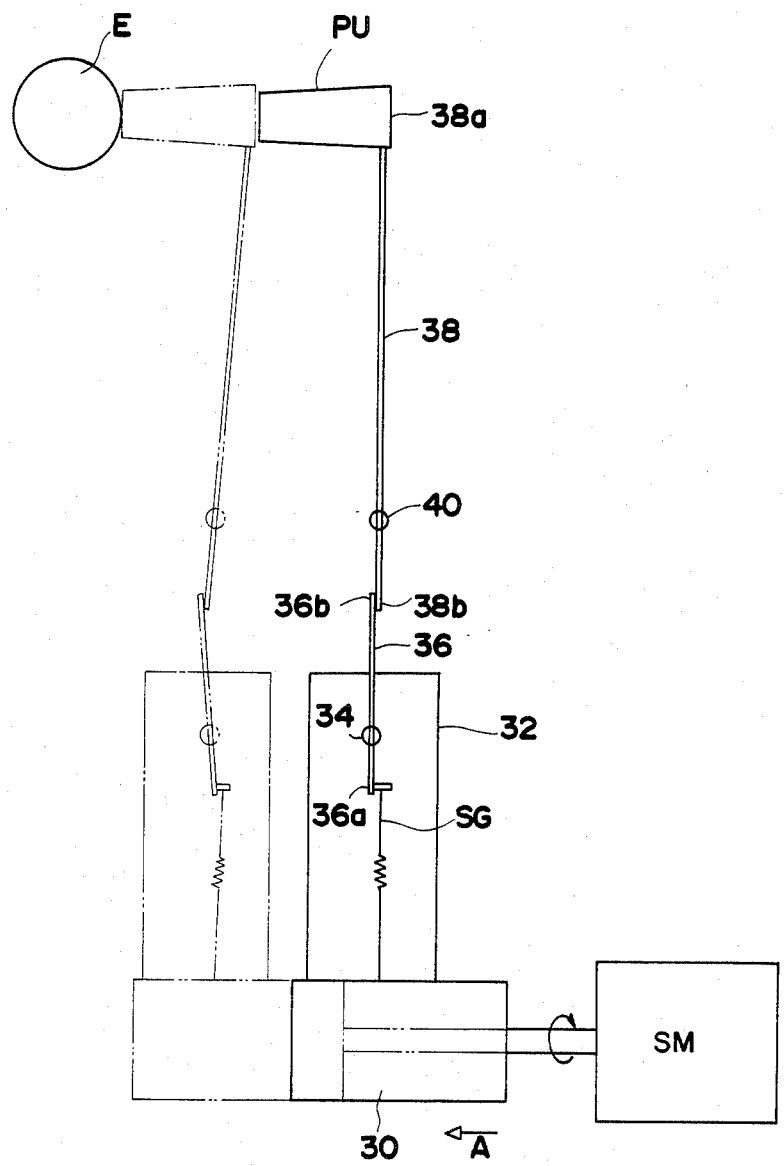
FIG. 5 is a simplified view showing the mechanical construction of the applanation device according to the first embodiment and the applanation pressure measuring means associated therewith.

Tonometers according to the present invention will now be described in detail with reference to the accompanying drawings. In all embodiments, the tonometers, unlike the conventional Goldmann tonometer adapted for measurement of intraocular pressure by naked eye inspection, are automatic tonometers wherein the subject's intraocular pressure is measured and the measured value itself is automatically indicated.

FIG. 4 shows the arrangement of an optical system for a tonometer in a first embodiment of the invention. In this figure, those components which act in the same way as the corresponding components shown in FIG. 1 are marked with like reference characters and a description thereof is omitted. In this embodiment, the lighting system (L) is exactly the same as the one shown in FIG. 1. However, the pickup (PU) has no prisms such as those shown at (16a), (16b) in FIG. 1, but instead a flat glass plate (20) for flattening the eyeball (E) and a pickup lens (22) are provided in the pick up. The pickup lens (22) is fixed in the pickup (PU) in such a manner that its focal plane coincides with the applanation surface, i.e., the front surface of the flat glass plate (20) which contacts the eyeball. The numeral (24) denotes a blue cut off filter for cutting off blue light; (26) denotes a relay lnes; and (28) denotes an image sensor.

The relay lens (26) is integrally fixed to said image sensor (28) so that its focal plane is located on the light-receiving surface of the image sensor (28). More particularly, the pickup lens (22) and relay lens (26) constitute image forming means (IF) whereby an image of a fluorescein ring formed around the surface to be flattened by the flat glass plate (20) is formed on the light-receiving surface of the image sensor (28). The focal plane of the pickup lens (22) is aligned with the applanation surface, while the focal plane of the relay lens (26) is aligned with the light-receiving surface of the image sensor (28). Furthermore, the lenses (22) and (26) have their optical axes aligned with each other. Therefore, even if the pickup (PU) is moved right and left as viewed in the figure to vary the applanation pressure against the eyeball (E) the image of the applanation surface is accurately formed on the light-receiving surface of the image sensor (28), with the image magnification remaining unchanged. Further, the blue cut off filter (24) serves to prevent the illuminating light from the lighting optical system (L) from entering the image sensor (28) to produce a noise.

Such arrangement ensures that an image of a fluorescein ring formed to surround the flattened surface is formed on the image sensor (28) by the pickup lens (22) and relay lens (26). After the image has been detected by the image sensor (28), the intraocular pressure value P (mm Hg) can be calculated on the basis of equation (1) from the area S (cm$^2$) surrounded with the fluorescein ring on the image sensor (28) and from the applanation pressure value W (g). As is clear from equation (1) in the present embodiment, when S=0.0735 cm$^2$=7.35 cm$^2$, P≈10 W.

Applanation means for flattening the eyeball (E) by the pickup (PU) and applanation pressure value measuring means will now be described with reference to FIG. 5. In FIG. 5 a stepping motor (SM) serves to move right and left a movable base (30) which supports the pickup (PU) while guiding said base by an unillustrated linear guide. A focus-electricity converter (32) is fixed on the movable base (30) and comprises a lever (36) turnable around the axis of a shaft (34), and a strain gauge (SG) which converts into an electric resistance a strain corresponding to the displacement of one end (36a) of said lever (36). A support lever (38) is fixed at one end (38a) to the pickup (PU) and contacted at the other end (38b) with the other end (36a) of the lever (36). The support lever (38) is rotatably supported on a shaft (40) fixed to the movable base (30).

As a result of such arrangement, during intraocular pressure measurement, the stepping motor (SM) is driven to move the movable base (30) to the left in the direction of arrow (A). The two levers (36) and (38) will not rotate until the pickup (PU) contacts the eyeball (E), whereupon the pickup (PU) is subjected to the reaction from eyeball (E), as indicated in dotted lines, causing a clockwise rotation of the support lever (38), which, in turn, causes a counterclockwise rotation of the lever (36), whereby the electric resistance value of the strain gauge (SG) is changed. That is, the force applied to the eyeball (E) is converted into electricity by the strain gauge (SG).

In the present embodiment, the length of the portion of the support lever (38) between the shaft (40) and the pickup (PU) is 10 times the length of the portion of the support lever (38) between the shaft (40) and the other and (38b), so that a force which is 10 times as great as the force applied to the eyeball (E) is measured by the strain gauge (SG). The electric signal corresponding to the change in the electric resistance value of the strain gauge (SG) is processed as a signal corresponding to the applanation pressure W on the eyeball (E).

Figure 6:
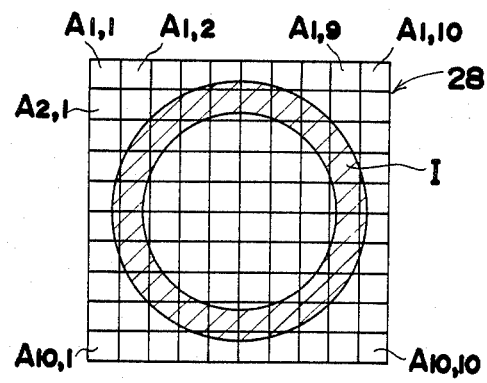
FIG. 6 is a front view showing the image of a fluorescein ring on the image sensor in the first embodiment.

A method of calculating the area of the flattened surface from the fluorescein ring image on the image sensor (28) will now be described with reference to FIG. 6. For the purpose of simplification of description, in FIG. 6, the image sensor is represented as an area image sensor having $10 \times 10$ micro-elements arranged as (A1,1) . . . (A10,10) as illustrated. The character (I) indicates a fluorescein ring image which is blurred owing to the bleeding of the fluorescein into the flattened surface and has a certain width. The image sensor is scanned first along a horizontal scanning line to produce successive outputs corresponding to the respective amounts of light received by the elements in the line A (1, n) where n = 1, 2 . . . 10, whereupon it is shifted in the vertical scanning direction to produce successive vertical scanning direction to produce successive outputs corresponding to the respective amounts of light received by the elements in the lines A (2,n), A (3,n), . . . A(10,n). The outputs from those elements which do not receive light from the fluorescein ring image (I) are low, while those elements which receive light from the fluorescein ring image (I) respectively produce outputs corresponding to the amounts of light received. A method of calculating the area surrounded by the fluorescein ring image (I) will be later described.

Figure 7:
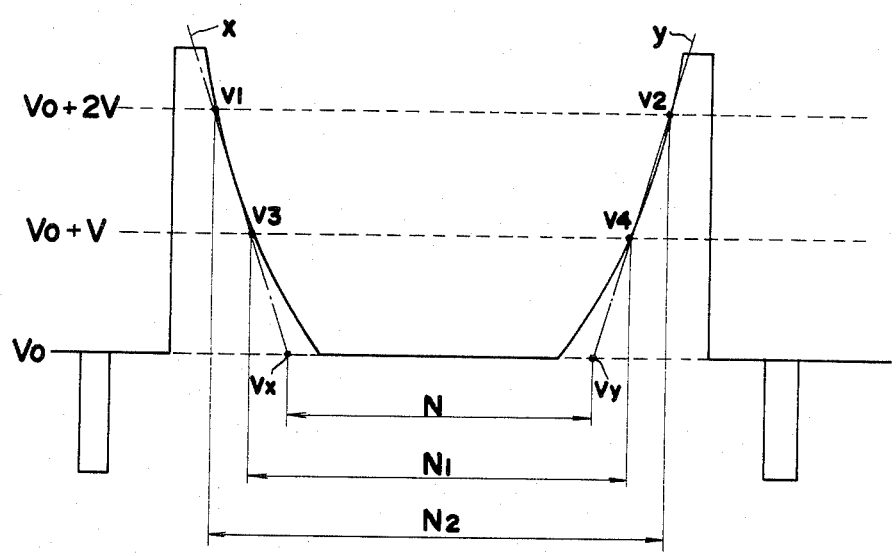
FIG. 7 is a graph explaining the procedure used for measuring the area enclosed by the fluorescein ring image in the first embodiment.

FIG. 7 shows the change of the video signal in one horizontal scanning line of the image sensor (28). A video signal during one horizontal scanning becomes like the one shown resulting from the bleeding of the fluorescein ring around the periphery of the flattened surface. As shown, the output of the region corresponding to the inner side of the flattened surface is taken to be a dark level $V_0$. In the present embodiment, the area surrounded by the fluorescein ring image is found as follows.

Two threshold levels $V_0+V$ and $V_0+2V$ ($V>0$) has been determined in advance. Supposed that the intersections between the video signal and the threshold level $V_0+2V$ are ($V_1$) and ($V_2$), and that the intersections between the video signal and the threshold level $V_0+V$ are ($V_3$) and ($V_4$), respectively. In this embodiment, the distance N which corresponds to the distance between the points ($V_x$) and ($V_y$) is treated as the transverse width of the fluorescein ring image along the horizontal scanning line. The point ($V_x$) is determined as the intersection between the dark level $V_0$ and a straight line X passed through both ($V_1$) and ($V_3$). The point ($V_y$) is determined as the intersection between the dark level $V_0$ and a straight line passing through both ($V_2$) and ($V_4$). Such a distance N is detected for every horizontal scanning line, by adding all these distances. Letting $N_2$ be the distance between ($v_1$) and ($v_2$) and $N_1$ be the distance between ($v_3$) and ($v_4$), then the distance N can be calculated from $N_1$ and $N_2$ approximately as $N = 2N_1 - N_2$.

Figure 8:
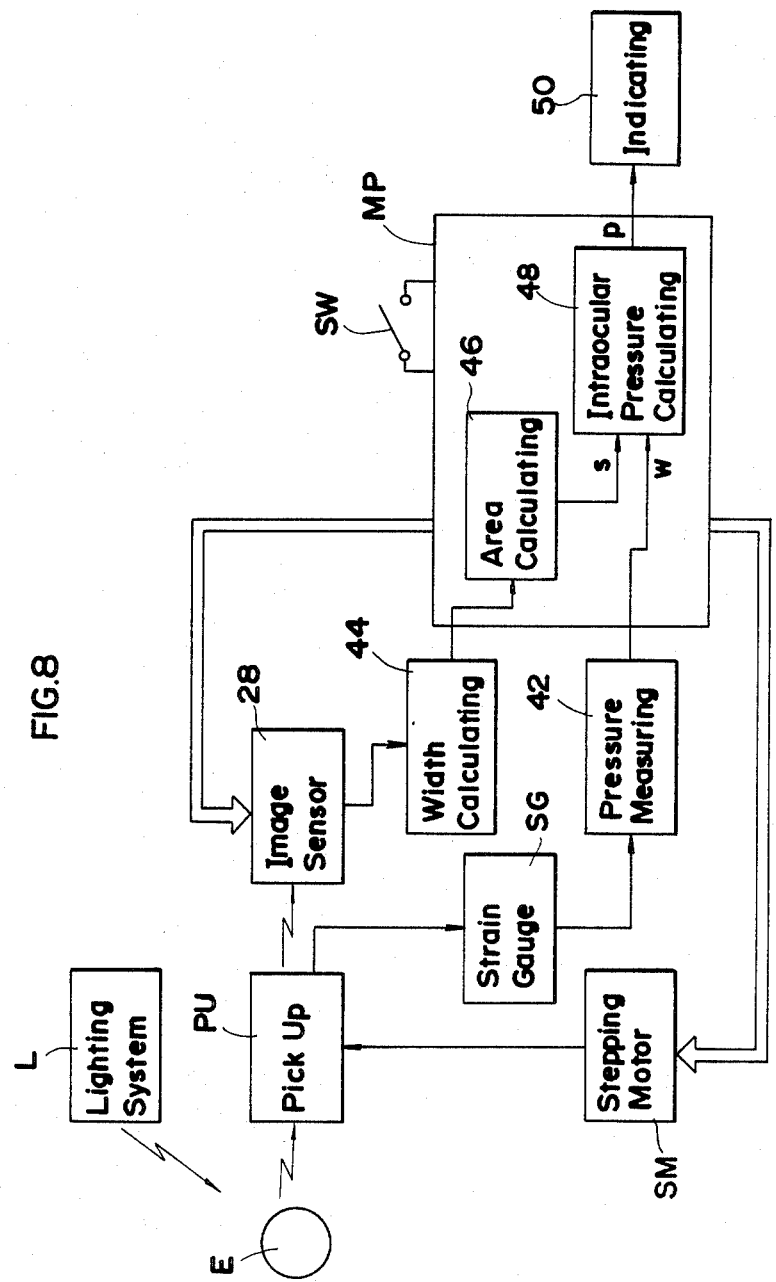
FIG. 8 is a block diagram showing the electric circuit in the first embodiment.

FIG. 8 is a block diagram showing the electric circuit of an automatic tonometer according to the present embodiment including the intraocular pressure measuring optical system of FIG. 4 and the applanation device of FIG. 5. The arrangement and operation of the apparatus of this embodiment will now be described. First, suppose that the lighting system (L) is illuminating the examined eyeball (E) with blue light. When the examiner closes a measurement start switch (SW), a microprocessor (MP) is operated, making the image sensor (28) operative, while the stepping motor (SM) is driven to move the movable base (30) to the left in FIG. 5. The examined person has his head fixed on a chin support, with fluorescein instilled into his eye, so that the eyeball (E) is prevented from moving. The stepping motor (SM) first moves the movable base (30) toward the eyeball (E) at high speed. An applanation pressure measuring circuit (42) memorizes the electric output $E_0$ of the strain gauge (SG) before the movable base (30) is moved.

When the pickup (PU) contacts the cornea of the eyeball (E), this means that the pickup (PU) receives the reaction from the eyeball (E), so that the output from the strain gauge (SG) changes. The microprocessor (MP) detects this output through the applanation pressure measuring circuit (42), and changes the rotative speed of the stepping motor (SM) to a lower one to move the movable base (30) at a lower speed if it detects the change of the output. The eyeball (E) is thus flattened by the pickup (PU). Then, the electric output from the strain gauge (SG) increases according to the increase of the applanation pressure on the eyeball. Since the periphery of the flattened surface is surrounded with fluorescein, an image of a fluorescein ring corresponding to the shape of the flattened surface is formed on the image sensor (28) through the pickup (PU). The video signal from the image sensor (28) is inputted into a transverse width calculating circuit (44) which, for each horizontal scanning line, detects the distance N corresponding to the transverse width of the fluorescein ring image such as the one described with reference to FIG. 7, and which converts it to a digital signal. The applanation pressure measuring circuit (42) detects the value obtained by subtracting $E_0$ from the electric output E of the strain gauge, and converts it into a digital output signal W. The area calculating circuit (46) in the microprocessor (MP) receives successive digital signals corresponding to the distance N concerning the individual scanning lines from the aforesaid transverse width calculating circuit (44), calculates the area surrounded with the fluorescein ring image from the sum of said digital signals in the vertical scanning direction and from the light-receiving area of each of the elements of the image sensor (28), and delivers a corresponding digital output S. This area corresponds to the area S of the flattened surface of the eyeball, and when the area S becomes 7.35 mm$^2$, the microprocessor (MP) delivers a stop signal to stop the stepping motor (SM). This area 7.35 mm is of a value determined within the range in which the ocular rigidity can be neglected.

The applanation pressure measuring circuit (42) measures the applanation pressure on the eyeball (E) in this state and delivers a corresponding digital output W. The intraocular pressure calculating circuit (48) in the microprocessor (MP) calculates the intraocular pressure P in this state from equation (1) using said S and W and delivers a corresponding output P. In the present embodiment, however, since it is so arranged that 10 times as great a force as the one applied to the eyeball is detected by the strain gauge (SG), W=10W, and when the area S of the flattened surface is 0.0735 cm$^2$, the relation $P \approx 10W$ holds between the applanation pressure W (g) on the eyeball and the intraocular pressure P (mmHg). Therefore, the result of measurement W by the applanation pressure measuring circuit (42) is used as the intraocular pressure P, making it unnecessary to perform complicated calculations. The intraocular pressure calculating circuit (48) delivers an electric output corresponding to the calculated intraocular pressure P, said electric output being transferred to an indicating circuit (50) which indicates the intraocular pressure P.

In addition, in the Goldmann tonometer, the intraocular pressure is measured only when the diameter of the fluorescein ring is 3.06 mm, and when the two semicircular images are shifted from the condition of contact depicted in FIG. 3(a) to the condition depicted in FIG. 3(b) or (c), the diameter of the flattened surface cannot be ascertained, with the result that the fluctions of intraocular pressure due to the beating of the subject's heart, that is, the maximum, minimum and mean intraocular pressure, for example, cannot be determined. In constrast, in the above embodiment, if the measurement of the area of the fluorescein ring is continued with the pressure to the eyeball maintained, this condition corresponds to the applanation pressure W in equation (1) being fixed, so that if the area S is found, the intraocular pressure P is obtained and hence the fluctuations of intraocular pressure due to the beating of the heart can be measured. More particularly, the area of the flattened surface S is measured and stored K times at predetermined time intervals by the microprocessor (MP) as Si (i=1, 2 . . . , K); the intraocular pressure obtained when the maximum area Smax is measured may be indicated as the minimum intraocular pressure Pmin, the intraocular pressure obtained when the minimum area Smin is measured may be indicated as the maximum intraocular pressure Pmax, and the average of all the intraocular pressures measured may be indicated as the mean intraocular pressure Pave. Alternatively, intraocular pressure may be measured at predetermined time intervals to enable the examiner to obtain said various intraocular pressure values from many intraocular pressure values successively indicated.

According to the present embodiment, the measurement of intraocular pressure is thoroughly automated, so that the examiner has only to close the measurement start switch (SW) and read the indicated values given by the indicating circuit (50). Thus, unlike the conventional Goldmann tonometer, it is no longer necessary for the examiner to perform the complicated operations of viewing through the finder (F) while applying pressure to the eyeball by manipulating the dial (14), finding the applanation pressure from the rotative position of the dial when the two semicircular images just contact each other, and multiplying said applanation pressure by 10 to find the intraocular pressure. Thus, the operation required for measuring the intraocular pressure using the present embodiment is very simple. Furthermore, in the Goldmann tonometer wherein since the fluorescein ring formed around the flattened surface is fairly blurred by the bleeding of the fluorescein instilled into the eye, the moment when the two semicircular images contact each other must be detected by naked eye inspection, and this detection requires a high degress of skill and is influenced by personal errors. In contrast, in the present embodiment, as already described with reference to FIG. 7, the blur of the fluorescein ring image is approximated by straight lines using two threshold levels and the detection requires no judgement or skill on the part of the examiner since the intraocular pressure value itself is displayed; it causes no personal error, so that precision measurement of intraocular pressure is possible. Further, the Goldmann tonometer is designed to measure intraocular pressure using the diameter of the fluorescein ring on the assumption that the flattened surface of the eyeball is circular. Thus, measurement error is involved unless the flattened surface is circular. Furthermore, if the examined eye has astigmatism, the special operation of turning the applanation pickup is required, as previously described. In the present embodiment, however, the area surrounded with the fluorescein ring is measured by the image sensor and intraocular pressure is measured on the basis of said area; thus, accurate measurement is always possible irrespective of the shape of the fluorescein ring without requiring any special operation, even if the examined eye has astigmatism.

Further, according to the present embodiment, the area of the flattened surface and the applanation pressure value can be measured and their variations can be ascertained. Thus, the maximum, minimum and mean intraocular pressure, which pressure, which has been impossible to measure by the Goldmann tonometer, can be determined and it is also possible to measure variations in intraocular pressure due to the beating of the heart. Further, in the Goldmann tonometer, accurate measurement cannot be made unless the relative position between the pickup (PU) and eyeball (E) is adjusted so that the boundary line between the prisms (16a) and (16b) passes through the center of the fluorescein ring. In contrast, in the present embodiment, the adjustment of the relative position between the pickup and the eyeball is simple since it is only necessary to form the image of the fluorescein ring on the image sensor.

A second embodiment of the invention will now be described. In the first embodiment shown in FIGS. 1 to 8, it is so arranged that applanation pressure on the eyeball is changed by linearly moving the movable base, as shown in FIG. 3, and if a stepping motor whose rotation can be accurately controlled is used, it is necessary to use means for converting the rotational motion produced by the stepping motor into a linear motion. This embodiment, however, uses an applanation device which does not require means for converting the rotational motion of the stepping motor into a linear motion.

Figure 9A:
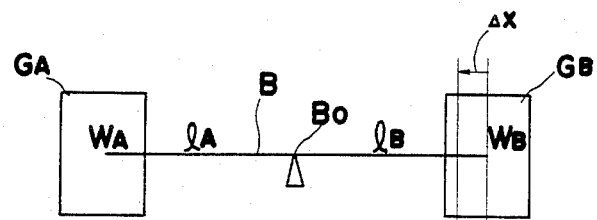
FIGS. 9(a), (b) and (c) and FIGS. 10(a), (b) and (c) are schematic views illlustrating the principle of the applanation device according to a second embodiment of this invention.
Figure 9B:
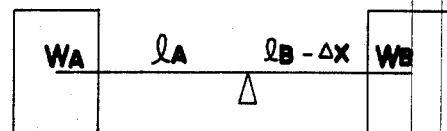
Figure 9C:
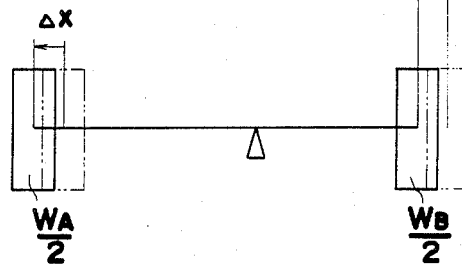

FIGS. 9(a)–(c) schematically shows the principle of the applanation device of the second embodiment. In FIG. 9(a) a support bar (B) with a weight ($G_A$) weighing $W_A$ fixed on one end and another weight ($G_B$) weighing $W_B$ placed on the other end of the bar is supported at a fulcrum ($B_O$) and is in balance. In this condition, the distance from the fulcrum ($B_O$) to the weight ($G_A$) is $l_A$ and the distance from the fulcrum ($B_O$) to the weight ($W_B$) is $l_B$.

FIG. 9(b) shows a condition in which the weight ($G_B$) has been moved a distance $\Delta x$ toward the fulcrum ($B_O$). In this condition, a counterclockwise rotation around the fulcrum ($B_O$) in a plane containing the paper. The rotational moment $M_1$ in this case is expressed by $$M_1 = W_A \cdot l_A - W_B(l_B - \Delta x).$$

Since $$W_A \cdot l_A = W_B \cdot l_B$$

$$M_1 = W_B \cdot \Delta x.$$

This embodiment is intended to press the eyeball by this rotational moment.

If the two weights ($G_A$) and ($G_B$) are equal in weight, this rotational moment $M_1$ can also be obtained by reducing the weights ($G_A$) and ($G_B$) by half and moving them together by $\Delta x$ to the left. This condition is shown in FIG. 9(c). The turning moment $M_2$ in the condition of FIG. 9(c) is expressed by $$M_2 = \frac{1}{2} W_A(l_A + \Delta x) - \frac{1}{2} W_B(l_B - \Delta x)$$

Further, $$W_A \cdot l_A = W_B \cdot l_B, \text{ and } W_A = W_B,$$

then, $$M_2 = W_B \Delta x = M_1$$

By moving the two weights by the same distance in the same direction in this manner, their respective weights can be reduced by half.

Figure 10A:
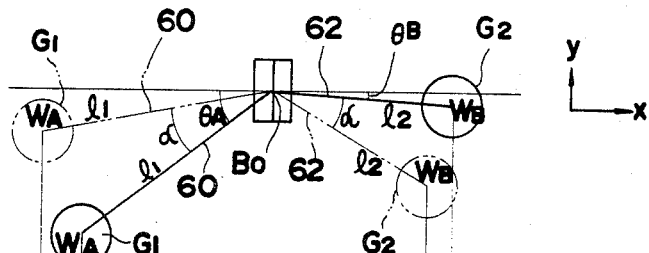
Figure 10B:
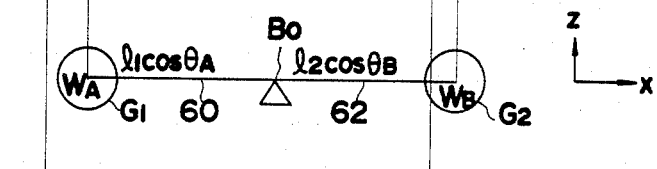

In this embodiment, in order to move the two weights ($G_A$) and ($G_B$) by the same distance in the same direction, the angle between two support bars each supporting the weights ($G_A$) or ($G_B$) is set less than 180° and said support bars are adapted to be rotated in a unit in a plane perpendicular to the paper. This will now be described with reference to FIGS. 10(a), (b) and (c). In FIGS. 10(a), (b) and (c), let us assume the plane in which the weights are rotated be xy-plane, in the plane in which a rotational moment is produced be xz-plane, the coordinate axes being determined as illustrated. FIG. 10(a) is a top view and FIG. 10(b) is a side view. The numeral (60) denotes a connecting bar with a weight ($G_1$) fixed in one end, and (62) denotes a connecting bar with a weight ($G_2$) fixed on one end, said connecting bars (60) and (62) being connected together and turnably supported on the fulcrum ($B_O$). In the condition shown in solid lines in FIG. 10(a), let $l_1$ and $l_2$ be the respective lengths of the connecting bars (60) and (62), ($W_A$) and ($W_B$) be the respective weight of the weights ($G_1$) and ($G_2$), and $\theta_1$ and $\theta_2$ be the respective angles the connecting bars (60) and (62) make with the x-axis, then the rotational moment $M_A$ around ($B_O$) in the xz-plane is expressed by $$M_A = W_A \cdot l_1 \cdot \cos \theta_A - W_B \cdot l_2 \cdot \cos \theta_B$$

If the two bars (60) and (62) are turned in a unit through an angle $\alpha$ in a clockwise direction to assume the condition shown in dotted lines in FIG. 10(a), the rotational moment $M_B$ in this condition is expressed by $$M_B = W_A \cdot l_1 \cos (\theta_A - \alpha) - W_B \cdot l_2 \cdot \cos (\theta_B + \alpha)$$

With attention paid to the x-direction, it is seem that thus situation indicates that the condition in which the weight ($G_1$) is located at a distance of $l_1 \cos \theta_A$ from the fulcrum ($B_O$) and the weight ($G_2$) is located at a distance of $l_2 \cos \theta_B$ from the fulcrum ($B_O$) has been shifted to the condition in which the weight ($G_1$) is located at a distance of $l_1 \cos (\theta_A - \alpha)$ from the fulcrum ($B_O$) and the weight ($G_2$) is located at a distance of $l_2 \cos (\theta_B - \alpha)$ from the fulcrum ($B_O$). Therefore, the rotational moment in the xz-plane changes. This embodiment utilizes this fact to change the pressure on the eyeball.

FIG. 11 shows an applanation device used in the second embodiment, the stepping motor (SM) is fixed on a base (100) and has its rotary shaft (102) integrally connected to an interlocking shaft (104). As shown in FIG. 12 which is a section view taken along the line XII—XII in FIG. 11, the interlocking shaft (104) is threadedly connected to an interlocking arm (106) through an adjusting nut (112) and a corrugated slip spring (113). When the adjusting nut (112) is rotated clockwise as viewed in FIG. 11, it is lifted to increase the slip effect of the corrugated spring (113), and reversely if it is rotated counterclockwise, it further presses the corrugated spring (113) to decrease the slip effect. That is, the nut (112) serves to adjust the slip effect between the interlocking shaft (104) and interlocking arm (106). Thus, in the condition with no force applied to the interconnecting arm (106), as will be later described, if pulses are transmitted to the stepping motor (SM), the rotary shaft (102), interlocking shaft (104) and interlocking arm (106) are rotated by an amount corresponding to the number of said pulses. Since the stepping motor (SM) is such that the number of pulses fed thereto accurately corresponds to the amount of rotation, it is possible to accurately detect the amount of rotation by counting the pulses.

It should be noted that, as shown in FIG. 13, a connecting member (108) rigidly secured to the base (100) and a support frame (110) to be described hereinafter is provided with a pair of stoppers (108a) and (108b) for limiting the angular range of rotation of said interlocking arm (106). And in the initial position shown in FIG. 11 and by dotted lines in FIG. 13, the interlocking arm (106) abuts against one of said stoppers (107a) and is thereby prevented from turning further in a counterclockwise direction. The normal rotational direction of the stepping motor (SM) is the clockwise direction indicated by the arrow (D) in FIGS. 11 and 13 and its reverse rotational direction is the counterclockwise direction. The other stopper (108b) is adapted to limit the clockwise rotation of the interlocking arm (106) due to the rotation of the stepping motor (SM) for the purpose of preventing application of an applanation pressure beyond a predetermined level to the eyeball. In the position indicated by solid lines in FIG. 13 where the interlocking arm (106) is abutted against the stopper (108b), the interlocking arm (106) has been turned through 40° from the initial position indicated by dotted lines in FIG. 13 and the applanation pressure to the eyeball in this position of interlocking arm (106) is 5 g.

In this position where the interlocking arm (106) is abutted against the stopper (108b) and thus prevented from turning in the clockwise direction, even if the stepping motor (SM) is driven in the clockwise rotational direction, the rotation is absorbed by a slip caused by the corrugated slip spring (113) between the interlocking shaft (104) and interlocking arm (106). This maximum applanation pressure of 5 g to the eyeball is set for ensuring a further safety to the eye. If the area of the flattened surface of the eyeball is not reached to a predetermined proper value by application of this pressure of 5 g to the eyeball, the intraocular pressure value is calculated with reference to the area under the pressure of 5 g. This operation will be described in detail hereinafter.

Returning to FIG. 11, the interlocking pins (114a) and (114b) are mounted on the interlocking arm (106). The interval between two arm segments of the interlocking arm (106) is variable so that the interval between said interlocking pins (114a) and (114b) may be adjusted. The interval between said pair of interlocking pins (114a), (114b) is controlled so that the pins engage therebetween a bearing (118) secured to a weight-supporting arm (116). Secured to one end of said weight-supporting arm (116) is a weight (120), while the other end of arm (116) is rigidly secured to a rotary frame (122). As shown in FIG. 12, the rotary frame (122) is rotatably mounted on a shaft (124a) which is rigidly mounted on a pickup holder (124). Secured to one end of a weight-supporting arm (128) is a weight (126) and the other end of arm (128) is secured to the rotary frame (122).

Rigidly secured to the pickup holder (124) is a pickup arm (130), one end of which carries a pickup (PU) rigidly secured thereto. A shaft (124a) of the pickup holder (124) is rigidly secured to a rotary holder (132). This rotary holder (132) carries a pair of rotary shafts (132a), (132b) rigidly mounted thereon and these rotary shafts (132a), (132b) are rotatably supported by a supporting frame (110). This part of the device is shown on exaggerated scale in the perspective view of FIG. 14 and in the longitudinal section view of FIG. 15. As shown in FIG. 14, the pair of weight-supporting arms (116), (128) are rotatable about the shaft (124b). Further, these weight-supporting arms (116), (128), rotary frame (122), pickup holder (124), pickup arm (130) and rotary holder (132) are rotatable as a unit about the rotary shafts (132a), (132b) in the direction of the arrow shown by R. As the pair of weight-supporting arms (116), (128) are rotated about the shaft (124a), the rotational moment around the rotary shafts (132a), (132b) is altered so as to change the pressure to the eyeball.

The rotary shaft (132a) extends through the supporting frame (110) externally and a subweight-mounting cylinder (134) is rigidly secured to the projection thereof. A side screw (136) is rigidly fixed to the subweight-mounting cylinder (134), extending in a direction opposite to the direction of pressure-increasing movement of the applanation pickup (PU) in a plane parallel to the plane of rotation of the applanation pickup arm (130). Threaded onto the side screw (136) is a subweight (138) and the rotation moment about the rotary shafts (132a), (132b) can be fine-controlled by adjusting the position of the subweight (138). This fine adjustment is necessary because when the applanantion device is mass-produced, there is inevitably a variation in the weight of weights (120) and (126), the length of the various members involved.

Now, the two weights (120), (126) are in balance in the initial position shown in FIG. 11, but if the pickup arm (130) is erect in this state, the pickup (PU) is swayed even by a slight movement of air to make initial setting of measurement difficult. Therefore, in this embodiment, setting is once made with the subweight (138) so as to bring the pickup arm (130) into an erect position and, then, the subweight (138) is shifted so that the pickup arm will be in a position slightly rotated forwardly from the erect position even in the initial state. Thus, in the initial state of this embodiment an applanation pressure value of 0.5 g has already been set.

Figure 16A:
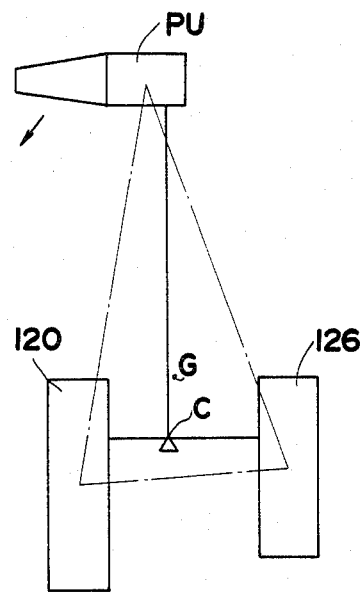
FIGS. 16(a) and (b) are schematic views explaining the relation between the center of rotation and the center of gravity of the pickup (PU)

Now, the position of rotary shafts (132a), (132b) and the position of the center of gravity of the total assembly of members rotated about the shafts will be explained with reference to FIG. 16(a), (b). The members rotated about the rotary shafts (132a), (132b) include the weights (120), (126), applanation pickup (PU), weight-supporting arms (116), (128), pickup arm (130) and so on but a predominant portion of the total weight is accounted for by the two weights (120), (126) and applanation pickup (130). Therefore, these members are assumed to represent the total weight of said assembly. Generally, it may be considered that their center of gravity (G) is preferably above the center of rotation (C) of rotary shafts (132a), (132b). Thus, if the center of gravity (G) is situated above the center of rotation (C) as depicted in FIG. 16 (a), as the rotation progresses in the direction of the arrowmark, the center of gravity (G) acts to increase the rotation moment because it operates to move in the more stable downward direction. In other words, as the applanation of the eyeball by the pickup (PU) progresses, the force generated by the vertically downward shift of the center of gravity (G), in addition to the rotation moment imparted by the stepping motor (SM), is applied to the eyeball, so that the difference between the applanation pressure value detected by counting the number of pulses inputted to the stepping motor (SM) and the pressure actually applied to the eyeball becomes greater with progress of applanation.

Figure 16B:
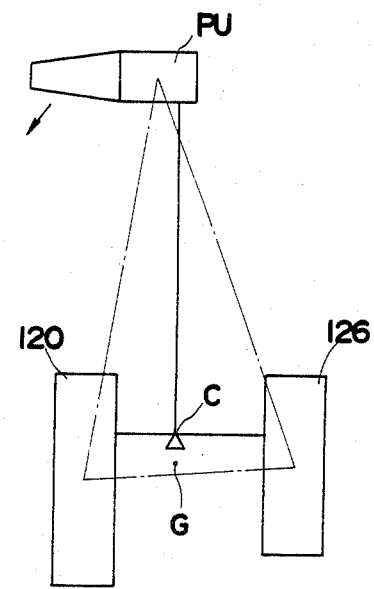

Conversely, if the center of gravity (G) is below the center of rotation (C) as depicted in FIG. 16(b), as the rotation progresses in the direction of the arrowmark, the center of gravity (G) acts to decrease the rotation moment because it also operates to move in the more stable downward direction. Thus, in order to return to the stable condition of the initial position, the center of gravity (G) generates a clockwise rotation moment opposite to the depicted counterclockwise rotation moment for applanationa and this clockwise rotation moment increases with the progress of applanation. In other words, as the difference between the pressure value detected by counting the number of pulses inputted to the stepping motor (SM) and the pressure actually applied to the eyeball increases with the progress of applanation.

The difference between these two centers can be a major error factor in the measurement of intraocular pressure as explained above. However, if the center of rotation (C) coincides with the center of gravity (G), the pickup arm (130) stands still even when the two weights (120), (126) are not in balance, so that it will be rather difficult to work with the device and find a balanced state. In this embodiment, therefore, the designs of the respective members as well as their layout have been determined so that the center of gravity (G) is situated slightly below the center of rotation (C) whereby a certain amount of error which will be negligible in terms of accuracy of measurement is preset in the setup.

Figure 17:
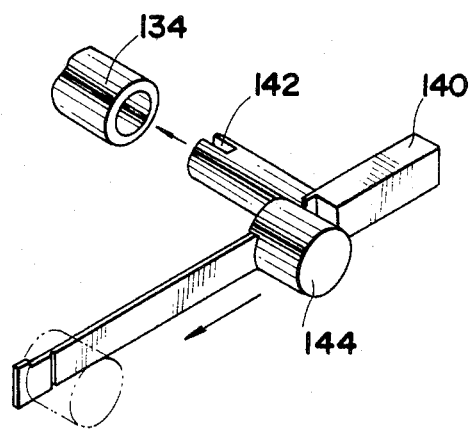
FIG. 17 is a perspective view showing a calibration element for the calibration performed in the second embodiment of the invention.

FIG. 17 is a perspective view showing an element used for calibration of the device according to this embodiment. A calibration element (140) has a slit (142) fitting a pin (not shown) located within a subweight-mounting cylinder (134) so that the calibration element (140) can be attached to the applanation device by causing the slit (142) of the element to engage the said pin. A calibration weight (144) is slidable as shown by the arrowmark and is capable of being stopped in the position indicated by dotted lines. When the calibration weight (144) is in the position indicated by solid lines, the calibration element (140) brings the pickup (PU) into a condition in which a pressure of 0.5 g has been applied in a direction opposite to the direction of applanation. Therefore, if the initial applanation pressure value in the initial state has been preset exatcly at 0.5 g, the pickup arm (130) stands erect and in equilibrium. If the pickup arm (130) does not stand erect, it is adjusted into the erect position by manipulating the subweight (138) shown in FIG. 11.

Then, the calibration weight (144) is slid in the direction of the arrowmark into the position indicated by dotted lines. In this state, the value of pressure applied to the pickup (PU) by the calibration element (140) is 2 g in the direction opposite to the direction of applanation. Therefore, if the number of pulses corresponding to this pressure value of 2 g is inputted to the stepping motor (SM) and if the pickup arm (130) stands erect, no adjustment is necessary.

In this embodiment, in the initial state shown in FIG. 11, the weight-supporting arm (116) supporting the weight (120) is situated on the xz plane including the applanation direction and the length of the weight-supporting arm (128) supporting the other weight (126) is equal to the length of the above-mentioned weight-supporting arm (116). Therefore, the weight (126) is heavier than the weight (120) and, a balanced condition is established in the state where in x dimension the weight (126) is closer to the fulcrum than is the weight (120).

The optical system of the entire tonometer according to this second embodiment is similar to that of the first embodiment described with reference to FIG. 4, and, therefore, will not be explained.

Figure 18:
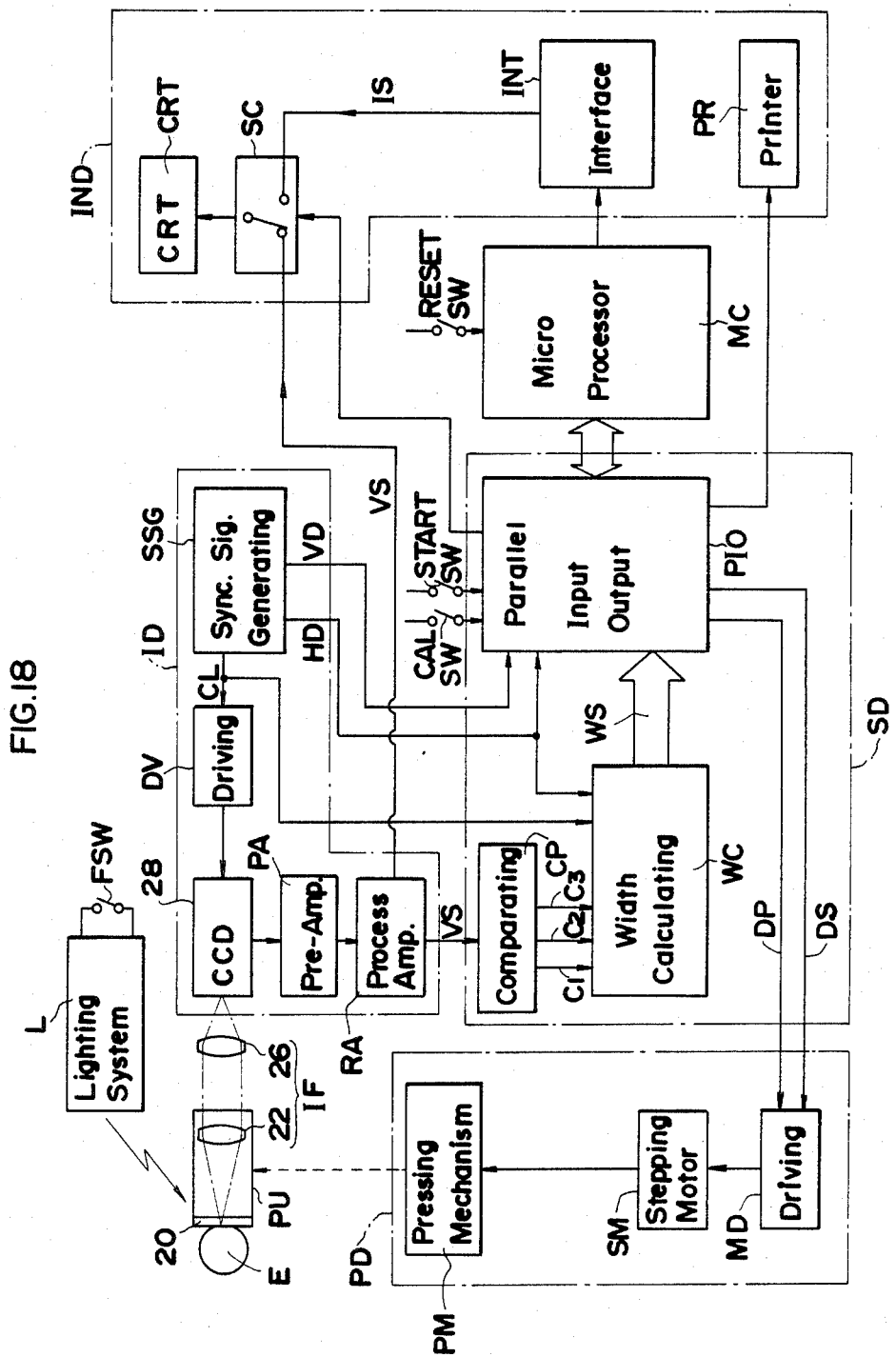
FIG. 18 is a block diagram showing the electric circuit of the second embodiment.

Now, the electric circuit of the whole of the second embodiment will be outlined by reference to the block diagram of FIG. 18. An image of the fluorescein ring formed around the flattened surface of the eyeball is formed on the CCD image sensor (28) by an image-forming optical system (IF). The size of the image is equal to that of the actual fluorescein ring. The image sensor (28) constitutes an image detector (ID) together with a synchronzing signal generating circuit (SSG) for generating a clock signal (CL), horizontal synchronizing signal (HD) and vertical synchronizing signal (VD), a drive circuit (DV) which drives the image sensor (28) at a timing based on the clock signal (CL), a preamplifier (PA) for amplifying the output of the image sensor (28), and a process amplifier (RA) which converts the output of said preamplifier to a video signal (VS). The video signal (VS) from the process amplifier (RA) is inputted to an indicating circuit (IND) and a width detection circuit (SD) for detecting the area surrounded with said fluorescein ring image. The drive circuit (DV) is adapted to generate a signal for driving the image sensor (28). The horizontal synchronizing signal (HD) and vertical synchronizing signal (VD) are respectively inputted to the width detection circuit (SD).

The width detection circuit (SD) has a comparation circuit (CP) which receives the video signal (VS) from the process amplifier (RA) and compares its voltage level with predetermined 3 reference levels, a width calculating circuit (WC) which calculates the transverse width of the fluorescein ring image per horizontal scanning line sequentially in accordance with the result of comparison, and a parallel input-output (PIO) which sends the signal concerning the width of the fluorescein ring image horizontal scanning line into a predetermined address in a microprocessor (MC) memory. The parallel input-output (PIO) also controls a switching circuit (SC) in the indicator (IND) in accordance with a signal from the microprocessor (MC) and controls the amount and direction of rotation of the stepping motor (SM) for shifting the applanation pickup (PU) in accordance with another signal from the microprocessor (MC). A calibration switch (CAL SW) is manually operated for calibration of the device and released when the intraocular pressure measurement is performed. A start switch (START SW) is a switch which is closed manually when the intraocular pressure measurement is commenced.

Though the parallel input-output (PIO), the microprocessor (MC) receives width signals (WS) from the width calculation circuit (WC) and the horizontal synchronizing signal (HD) and vertical synchronizing signal (VD) from the synchronizing signal generating circuit (SSG). The width signals (WS) are sequentially stored at predetermined addresses in the microprocessor (MC) memory. Based on the signals thus stored, the microprocessor (MC) calculates the area of the flattened surface of the eyeball. As will be described in detail, the microprocessor (MC) calculates the maximum, mimimum and mean intraocular pressures according to the calculated area and the corresponding applanation pressure value. A signal corresponding to each calculated intraocular pressure value is fed to an interface circuit (INT) and also fed via said parallel input-output (PIO) to a printer (PR) where it is printed. Moreover, in order to control the applanation pressure of the pickup (PU) against the eyeball in accordance with the calculated area, the microprocessor (MC) controls the amount and direction of rotation of the stepping motor (SM). The number of drive pulses (DP) corresponding to the amount of rotation of the stepping motor (SM) and a direction signal (DS) signifying the direction of rotation are transmitted from the microprocessor (MC) through the parallel input-output (PIO) to a motor driving circuit (MD) whereby the amount and direction of rotation of the stepping motor (SM) are controlled in accordance with the two signals. A reset switch (RESET SW) is manually closed, when a measurement or a calibration procedure has been completed and another measurement is to be commenced, for resetting the entire device to the initial state.

The stepping motor (SM), its drive circuit (MD) and a pressurizing mechanism (PM) shown in FIG. 11 constitutes an applanation device (PD) of FIG. 18.

The video signal (VS) from the process amplifier (RA) and a character signal (IS) from the interface circuit (INT) are both inputted to the switching circuit (SC) and as the video signal (VS) is selected by the parallel input-output (PIO), the image on the image sensor (28) is reproduced on a CRT display (CRT). As the character signal (IS) is selected by the parallel input-output (PIO), the data such as the maximum, minimum and mean intraocular pressures are displayed in characters on the CRT display (CRT). On the the calibration mode with the calibration switch (CAL SW) in ON position, the applanation pressure value appears on the CRT display (CRT). The CRT display (CRT), switching circuit (SC), interface circuit (INT) and printer (PR) constitutes the indicating circuit (IND).

A lighting system (L) includes a light source (2) comprising a tungusten lamp as illustrated in FIG. 4. On closure of a footswitch (F SW) with a main switch (not shown) closed, the light source (2) is started to illuminate a applanation surface.

Figure 19:
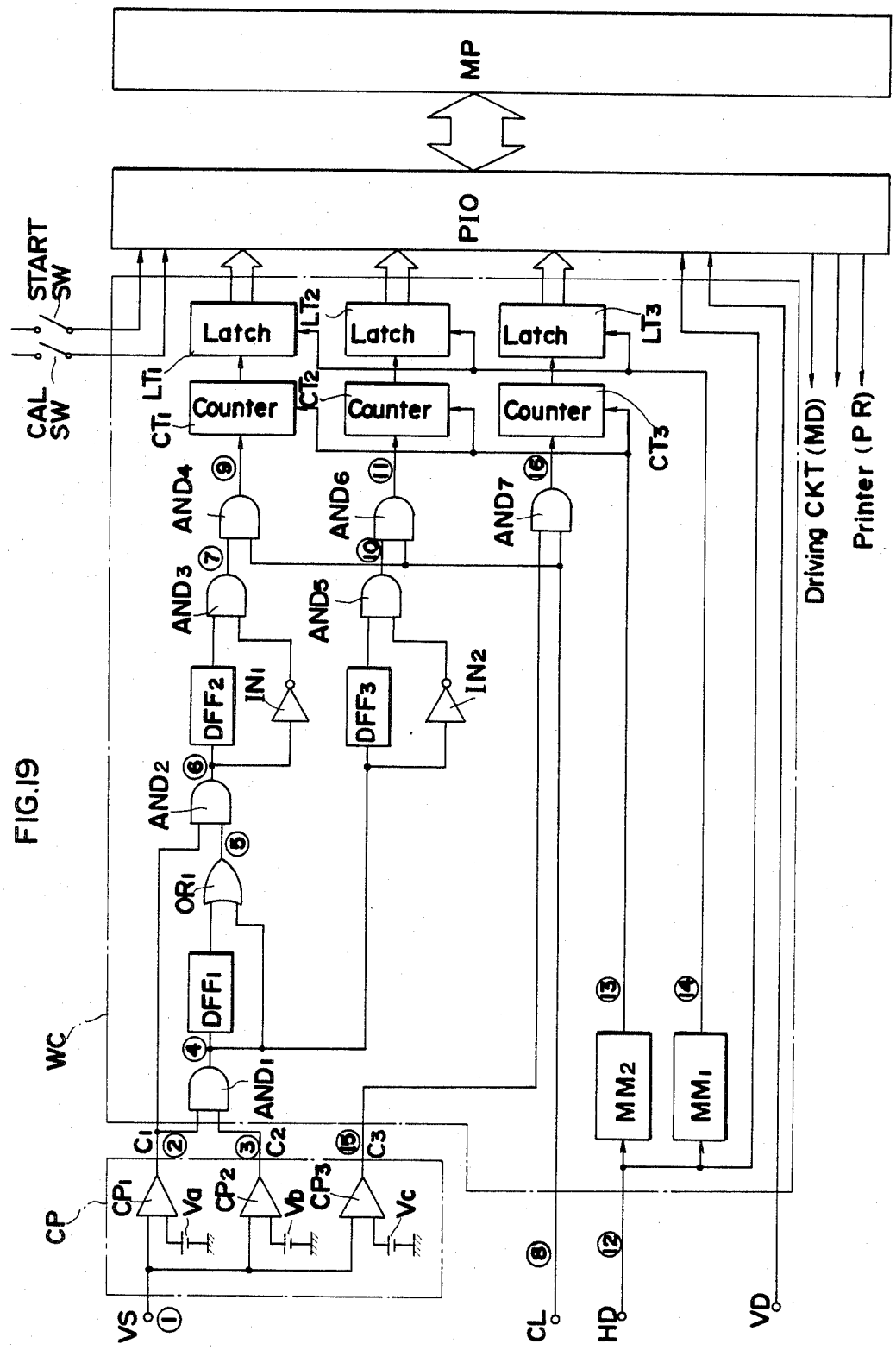
FIG. 19 is an electric circuit diagram showing an area detection circuit thereof.
Figure 20:
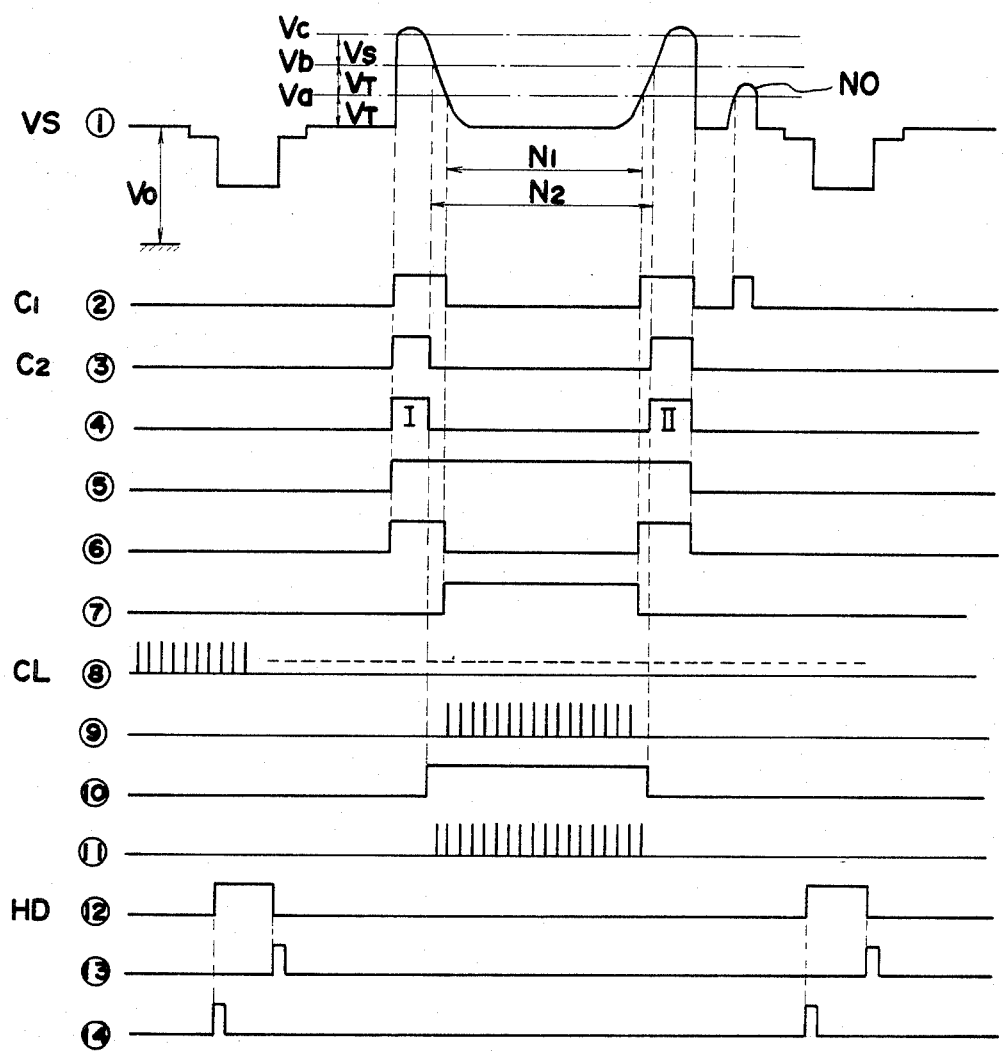
FIG. 20 is a timing chart showing the changes of signals at respective points of FIG. 19.

The construction of the width detection circuit (SD) will be described in detail by reference to the electric circuit diagram of FIG. 19. The changes of output voltages at the designated points in FIG. 19 are shown in the time chart of FIG. 20. FIG. 20 is a time chart showing the changes of output voltages corresponding to one horizontal scan traversing the center of the fluorescein ring image. Here, as in the first embodiment, the approximation of $N=2N_1-N_2$ is used to calculated the transverse width N of the fluorescein ring image. Here, $N_1$ and $N_2$ are as shown in FIG. 20.

As shown in FIG. 19, the video signal (VS) from the process amplifier (RA) is fed to the comparation circuit (CP). The comparation circuit (CP) includes three comparators (CP$_1$), (CP$_2$) and (CP$_3$) and three reference power sources having different voltage levels (Va), (Vb) and (Vc). As shown in FIG. 20, the voltage levels (Va), (Vb) and (Vc) of these reference power sources are predetermined to satisfy the following relations.

$$V_a = V_O + V_T$$

$$V_b = V_O + 2V_T$$

$$V_c = V_O + 2V_T + V_S$$

where $V_O$: dark level of image sensor (28)
$V_T$, $V_S$: predetermined constant voltages As the comparator (CP$_1$) outputs a HIGH level when the video signal (VS) is higher than the voltage $V_a$, it shows an output change as shown at 2 in FIG. 20.

Incidentally, the peak (NO) shown at 1 in FIG. 20 is a noise due to fluorescein. The output C$_2$ of the comparator (CP$_2$) is at HIGH level when the video signal (VS) is higher than the voltage $V_b$, it shows the time-chart indicated at 3 in FIG. 20. The outputs C$_1$ and C$_2$ of these two comparators (CP$_1$) and (CP$_2$) are both inputted to an AND circuit (AND$_1$), the output of which changes as shown at 4 in FIG. 20. The output of the AND circuit (AND$_1$) is used as a video signal (VS) over the voltage $V_b$. This is for eliminating the electrical noise included in the output of the comparator (CP$_2$).

The output of the AND circuit (AND$_1$) is inputted to an OR circuit (OR$_1$) via a D-flip-flop (DFF$_1$) and, at the same time, directly to the OR circuit (OR$_1$). Therefore, as shown in FIG. 20(5), the output of the OR circuit (OR$_1$) is at HIGH level from the positive edge of a first square wave (I) to the negative edge of a second square wave (II). As this output of the OR circuit (OR$_1$) and the output (C$_1$) of the comparator (CP$_1$) are inputted to the AND circuit (AND$_2$), the output of the AND circuit (AND$_2$) is as shown at 6 in FIG. 20. The output of the AND circuit (AND$_2$) is used as a video signal over the voltage $V_a$. This is for removing the electrical noise included in the output of the comparator (CP$_1$) and for removing the noise (NO) due to the fluorescein deposited in any position external of the fluorescein ring on the flat glass at the top of the pickup (PU).

As the output of the AND circuit (AND$_2$) is inputted to the AND circuit (AND$_3$) via the D-flip-flop (DFF$_2$) and inverter (IN$_1$) respectively, the output of the AND circuit (AND$_3$) changes as indicated at 7 in FIG. 20. The time during which the output of the AND circuit (AND$_3$) is at HIGH level corresponds to the inner diameter of the fluorescein ring image at the voltage $V_a$ as the threshold level. Thus, it corresponds to the interval N$_1$ in FIG. 7. The output of the AND circuit (AND$_3$) is fed to one of input terminals of and AND circuit (AND$_4$). As the other input terminal of this AND circuit (AND$_4$) is supplied with a clock signal (CL) from the synchronizing signal generating circuit (SSG) as indicated at 8 in FIG. 20, the AND circuit (AND$_4$) outputs the number of clock pulses corresponding to said interval N$_1$ as indicated at 9 in FIG. 20. This number of pulses N$_{1,k}$ is counted by a counter (CT$_1$).

The output of the AND circuit (AND$_1$) is inputted to an AND circuit (AND$_5$) independently via D-flop-flop (DFF$_3$) and inverter (IN$_2$) respectively. As shown at 10 in FIG. 20, the output of the AND circuit (AND$_5$) is at HIGH level from the negative edge of the first square wave (I) through the positive edge of the second square wave (II). The time during which the output of this AND circuit (AND$_5$) is at a HIGH level corresponds to the inner diameter of the fluorescein ring image at the voltage $V_b$ as the threshold level, i.e. the interval N$_2$. As the AND circuit (AND$_6$) is supplied with the output of the AND circuit (AND$_5$) and the clock signal (CL), it outputs the number of clocks pulses corresponding to the above-mentioned interval N$_2$ shown at 11 in FIG. 20. This number of clock pulses N$_{2,k}$ is counted by a counter (CT$_2$). Since the clock signal from the synchronizing signal generating circuit (SSG) corresponds to each element of the image sensor in a ratio of 1:1 and the size of each element is known, the intervals N$_1$ and N$_2$ can be learned by counting the above-mentioned number of clock pulses.

In this embodiment, fluorescein (FL) is first attached to the front surface of the glass plate (20) of the pickup (PU) and instilled into the eye thereby. The comparator (CP$_3$) is provided for checking the amount and concentration of fluorescein (FL) applied to the front surface of said glass plate (20). The procedure for applying fluorescein to the front of the flat glass (20) and checking its amount and concentration prior to applanation will now be explained by reference to FIG. 19 and the time chart of FIG. 21.

Figure 21:
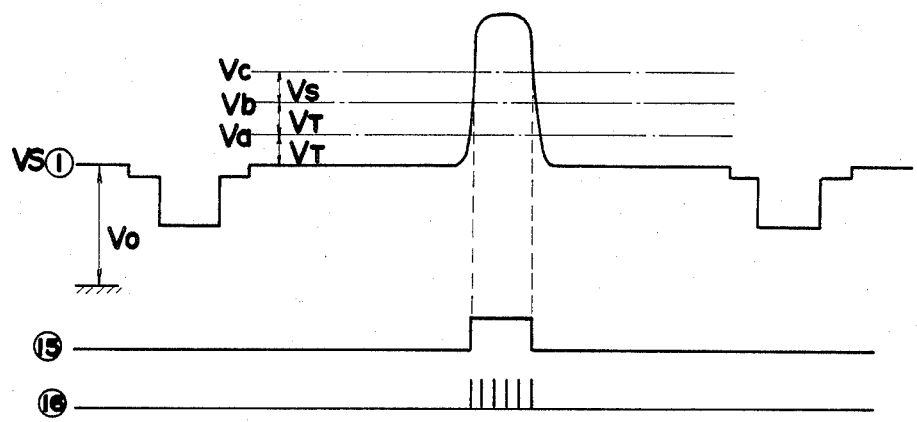
FIG. 21 is a timing chart showing changes of signals at respective points at fluorescein check.

FIG. 21 is a time chart showing the case in which the amount and concentration of fluorescein (FL) on the front surface of said flat glass (20) are both adequate. As shown at 1 in FIG. 21, when the concentration of fluorescein (FL) is sufficient, the peak of video signal (VS) is over the voltage level $V_c$. Therefore, as shown at 15 in FIG. 20, the output C$_3$ of the comparator (CP$_3$) is at HIGH level when the video signal (VS) is over the voltage $V_c$. Thus, the voltage level $V_c$ of the reference power source ($V_c$) is predetermined so that when the concentration of fluorescein (FL) is sufficient, the video signal (VS) is over the voltage $V_c$.

The output $C_3$ of the comparator ($CP_3$) is inputted to an AND circuit ($AND_7$) which is also suppled with the clock signal (CL). Therefore, as shown at 16 in FIG. 21, the AND circuit ($AND_7$) outputs the number of pulses corresponding to the time during which the output of the comparator ($CP_3$) is at HIGH level and this number $N_{3,k}$ is counted by a counter ($CT_3$). This number of clock pulses $N_{3,k}$ corresponds to the width of fluorescein (FL) applied to the front surface of the glass plate (20). This number is utilized for judging whether the amount of fluorescein (FL) applied is proper or not.

Referring, back to FIGS. 19 and 20, a monostable multivibrator ($MM_2$) outputs a square pulse, as indicated at 14 in FIG. 20, in accordance with the positive edge of the horizontal synchronizing signal (HD) shown in FIG. 20. This square pulse is inputted into latch circuits ($LT_1$), ($LT_2$) and ($LT_3$), which on reception of the square pulse, latch the counts $N_{1,k}$ $N_{2,k}$ and $N_{3,k}$ of counters ($CT_1$), ($CT_2$) and ($CT_3$), respectively. The signals relating to the latched count values $N_{1,k}$ $N_{2,k}$ and $N_{3,k}$ are inputted to the microprocessor (MC) via the parallel input-output (PIO) and are stored in predetermined memory addresses $A_{1,k}$ $A_{2,k}$ and $A_{3,k}$ respectively.

The monostable multivibrator ($MM_1$) outputs a square pulse, as indicated at 13 in FIG. 20, in accordance with the negative edge of the horizontal synchronizing signal (HD). This square pulse is inputted to the counters ($CT_1$), ($CT_2$) and ($CT_3$) and the counters are respectively reset.

Now, as will be seen from FIG. 20, the video signal (VS) shows a sudden change at the outer margin of the fluorescein ring image, suggesting that there is substantially no bleeding of fluorescein (FL). This is because, owing to its surface tension, the fluorescein (FL) rises up substantially rectilineally from the glass plate (20) to reach the eyeball and its height from the surface of the glass plate (20) is approximately maximal. Therefore, the timing of positive edge of the first square wave and the timing of negative edge of the second square wave (II) are nearly fixed, irrespective of whether the voltage $V_a$ is used as the threshold level or the voltage $V_b$ is used as the threshold level.

Referring, again, to FIG. 18, the microprocessor (MC) receives the horizontal synchronizing signal (HD) and vertical synchronizing signal (VD) from the synchronizing signal generating circuit (SGG) via the parallel input-output (PIO) and, also, the width signals (WS) relating to the widths along the horizontal scanning lines from the width calculation circuit (WC). Moreover, the microprocessor (MC) receives a calibration signal outputted on closure of the calibration switch (CAL SW) via the parallel input-output (PIO) and a start signal which is outputted on closure of a start switch (START SW). A reset switch (RESET SW) is manually operated and outputs a reset signal on closure. As this reset signal is inputted to the microprocessor (MC), the latter is reset to its initial state.

When the vertical synchronizing signal (VD) from the synchronizing signal generating circuit (SSG) becomes HIGH and, then, Low, the count value $N_{1,k}$ $N_{2,k}$ and $N_{3,k}$ then latched in the latch circuits ($LT_1$), ($LT_2$) and ($LT_3$) shown in FIG. 19 are stored in predetermined respective addresses $A_{1,0}$ $A_{2,0}$ and $A_{3,0}$ of the microprocessor (MC) memory. Then, the microprocessor (MC) is brought into a HALT condition and, thereafter, each time a vertical synchronizing signal (VD) is inputted, sequentially stores the count values $N_{1,K}$, $N_{2,K}$, $N_{3,K}$ latched in the respective latch circuits ($LT_1$), ($LT_2$) and ($LT_3$) in predetermined addresses $A_{1,K}$, $A_{2,K}$, $A_{3,K}$ (K=0, 1, 2, ... M).

Figure 23A:
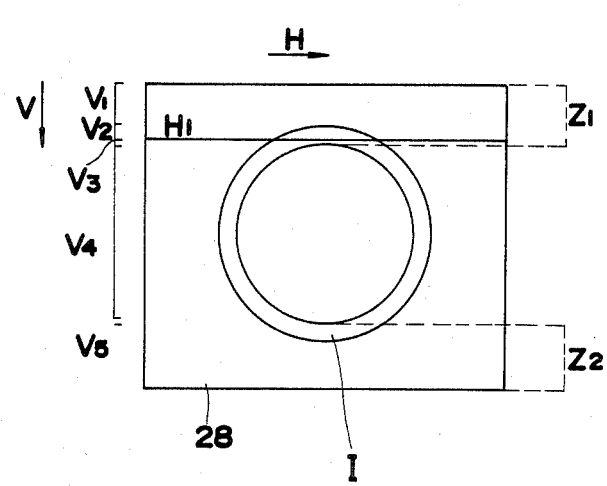
FIGS. 23(a), (b) each is a sketch for explanation an error signal from the area detection circuit.
Figure 23B:
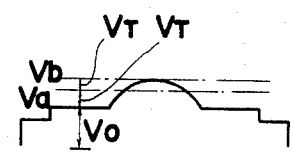

After the count value information for all the horizontal scans has been memorized, the microprocessor (MC) calculates the area confined by the fluorescein ring image according to a predetermined program. The flow chart of this program is shown in FIG. 22 and the flow will now be explained below. In this embodiment, the fluorescein ring image (I) is formed on the image sensor (28) as shown in FIG. 23(a) and, therefore, assuming that the direction of horizontal scanning is H and the direction of vertical scanning is V, the video signal from a horizontal scan does not form a definite double-peak structure in the ($Z_1$) and ($Z_2$) regions. By way of illustration, the video signal along the horizontal scanning line ($H_1$) is as illustrated in FIG. 23(b). In such a case, the count numbers corresponding to the region outside of the fluorescein ring image (I) would be mistakenly stored in memory. Therefore, the microprocessor (MC) is so constructed as to reject such errorneous count numbers and to calculate only the sum of count numbers corresponding to the elements located internally of the fluorescein ring image (I).

At the addresses $A_{1,0}, A_{1,1}, \ldots A_{1,M}$ in the memory of the microprocessor (MC), the count numbers $N_{1,K}$ (K=0, 1, ... M) corresponding to the respective horizontal scanning lines have been stored.

In the flow chart of FIG. 22, the contents stored at memory addresses $A_{1,0}, A_{1,1} \ldots A_{1,M}$ are represented as $(A_{1,0}), (A_{1,1}) \ldots (A_{1,M})$, respectively. As the program is started, K=1 is set as an initial value in step $F_1$ in the first place. Then, in step $F_2$, $Q_{1,K} = |(A_{1,K}) - (A_{1,K-1})|$ is calculated and in step $F_3$ it is judged if this $Q_{1,K}$ is smaller than a predetermined value $\alpha$ which is to be explained hereinafter. If $Q_{1,K}$ is larger than $\alpha$, the data $(A_{1,K})$ in memory address $A_{1,K}$ is replaced with $(A_{1,K-1})$ in step $F_4$. When $Q_{1,K}$ is smaller than $\alpha$, the data $(A_{1,K})$ is retained in the memory address $A_{1,K}$ as shown in step $F_5$. Thereafter, in step $F_6$, K is replaced with K+1. The program sequence of steps $F_2$ through $F_6$ is repeatedly executed until the new value of K reaches M.

This program of steps $F_2$ through $F_6$ is intended to reject the above-mentioned information on the picture elements located outside of the fluorescein ring image. This utilizes the fact that in a single picture, the data $(A_{1,K})$ varies in the following manner, provided that the direction of horizontal scanning (H) and that of vertical scanning (V) of the image sensor (28) are set as shown in FIG. 23(a) and that the image sensor (28) sequentially performs a horizontal scanning of the uppermost row of elements and outputs the outputs of those elements and after a making one vertical scan, performs another horizontal scanning of the next horizontal row of elements and outputs of those elements in sequence.

(1) The data $(A_{1,K})$ relating to the horizontal scanning lines within the region ($V_1$) not receiving the fluorescein ring image at all is zero.

(2) The data $(A_{1,K})$ relating to the horizontal scanning lines passing through the region ($V_2$) receiving only the outer margin of the fluorescein ring image is a fairly large value.

(3) The data $(A_{1,K})$ relating to the horizontal scanning lines within the regions $(V_3)$ adjoining to the inner margin of the fluorescein ring image is near zero.

(4) Regarding the region $(V_4)$ of horizontal scanning lines traversing the fluorescein ring image, the data $(A_{1,K})$ increases gradually by small degrees with the progress of vertical scanning and, after passing the center of the fluorescein ring image, decreases gradually by degrees.

(5) At the position $(V_5)$ where the horizontal scanning lines leaves the inner margin of the fluorescein ring image, the data $(A_{1,K})$ becomes considerably greater than the data $(A_{1,K})$ relating to the immediately preceding horizontal scanning line.

The predetermined value $\alpha$ mentioned herein has been set by utilizing the above phenomena (1) through (5), as follows. First, the data $(A_{1,K})$ is zero as far as horizontal scanning lines apart from the fluorescein ring image are concerned. As the horizontal scanning line adjoins the outer margin of the fluorescein ring image for the first time, the data $(A_{1,K})$ is the count number of clock signals corresponding to the distance from the approximate center of the picture in the horizontal direction to the end thereof, thus being a fairly large value. The predetermined value $\alpha$ is set as a value less than the above value. Thus, when the horizontal scanning line first adjoins the fluorescein ring image, there holds the following relation in step $F_3$.

$$Q_{1,K} = |(A_{1,K}) - (A_{1,K-1})| = |(A_{1,K})| > \alpha$$

Then, the sequence proceeds to step $F_4$, where the data in memory address $A_{1,K}$ is replaced with $(A_{1,K-1})$, i.e. zero.

Thereafter, with the progress of vertical scanning and until the horizontal scanning line reaches the inner margin of the fluorescein ring image, the data $(A_{1,K})$ becomes gradually smaller but the predetermined value of $\alpha$ has been set so that the following relation still holds.

$$Q_{1,K} = (A_{1,K}) > \alpha$$

This is a first condition of said predetermined value $\alpha$.

When the horizontal scanning line just adjoins the inner margin of the fluorescent ring image, the data $(A_{1,K})$ relating to this horizontal line assumes a value close to zero. The predetermined value $\alpha$ is set so that the following relation holds at this stage.

$$Q_{1,K} < \alpha$$

This is a second condition of the predetermined value $\alpha$. In this state, as shown in step $F_5$, the data $(A_{1,K})$ is retained in the memory address $A_{1,K}$.

With a further progress of scanning in the vertical direction, while the horizontal scanning line traverses the fluorescein ring image, the data $(A_{1,K})$ increases by small degrees and, then, decreases by small degrees. The predetermined value $\alpha$ is set so that the following relation holds during this stage.

$$Q_{1,K} < \alpha$$

This is a third condition of $\alpha$.

When the horizontal scanning lines passes through the lowermost region of the inner margin of the fluorescein ring image (I) shown in FIG. 23(a), the data $(A_{1,K})$ is a value close to zero but it becomes a fairly large value as the horizontal scanning line leaves the inner margin. The predetermined value $\alpha$ is set so that the following relation holds in this stage.

$$Q_{1,K} > \alpha$$

This is a fourth condition of $\alpha$. Thus, $\alpha$ is set so as to satisfy the above first through fourth conditions.

Immediately after the horizontal scanning line has left the inner margin of the fluorescein ring image, the data $(A_{1,K})$ is replaced with $(A_{1,K-1})$, that is to say it is replaced with a value close to zero. This value is so small that it can be disregarded in the subsequent calculation. Since the data $(A_{1,K})$ corresponding to the horizontal scanning line which has left the outer margin of the fluorescein ring image is zero, $$Q_{1,K} < \alpha$$

And the data $(A_{1,K})$ is left as it is in the memory address $A_{1,K}$.

As the program for rejecting the count number data relating to the region outside of the fluorescein ring image has been executed on all of the data $(A_{1,0})$, $(A_{1,1})$, ..., $(A_{1,M})$ corresponding to all horizontal scanning lines, $K = M$ is detected in step $F_7$. Then, the sequence proceeds to step $F_8$ and $$N_1 = \sum_{K=0}^{M} (A_{1,K})$$

is calculated.

Steps $F_9$ through $F_{16}$ represent a program which performs exactly the same calculations for the data $(A_{2,0})$, $(A_{2,1})$ ..., $(A_{2,M})$ on count numbers $N_{1,K}$ ($K=0$, 1, 2, ..., M) stored in the addresses $A_{2,0}$, $A_{2,1}$, ..., $A_{2,M}$ of the memory as those described for steps $F_1$ through $F_8$.

In step $F_{16}$, as in step $F_8$, $$N_2 = \sum_{K=0}^{M} (A_{2,K})$$

is calculated.

Finally, in step $F_{17}$, the area of the flattened surface S is calculated by means of the formula.

$$S = \beta(2N_1 - N_2)$$

Where $\beta$ is a constant which is determined by the ratio of the actual area of the flattened surface to the area of the fluorescent ring image on the image sensor (28) and by the size of respective elements of the image sensor (28). Therefore, the area S of the flattened surface can be calculated by multiplying the data $(2N_1 - N_2)$ on the number of elements corresponding to the area confined by the fluorescent ring image by the constant $\beta$. The count numbers $N_{3,K}$ ($K = 0, 1, ..., M$) for checking the concentration and amount of fluorescein have been stored as $(A_{3,0})$, $(A_{3,1})$, ..., $(A_{3,M})$ at the addresses $A_{3,0}$, $A_{3,1}$, ..., $A_{3,M}$ of the memory. Since the circuit for calculating this count number $N_{3,K}$ outputs the number of clock signals corresponding to the video signal (VS) exceeding the voltage $V_3$, the area $S_D$ of the fluorescein (FL) spot in the presence of adequate amount and concentration of fluorescein (FL) is calculated by means of the formula.

$$S_D = \beta \cdot \sum_{K=0}^{M} (A_{3,K})$$

Then, the manner of microprocessor (MC) control of each circuit will be explained by reference to the flow charts of FIGS. 24 and 25. First, as a main switch (not shown) is closed, the microprocessor (MC) sets the device in its initial condition as shown in step $ST_1$. Thus, interlocking arm (106) moves counterclockwise as viewed in FIG. 11 through 40 degrees. This is accomplished by feeding the number of drive pulses (DP) corresponding to the said 40 degrees and a direction signal (DS) showing the direction of reverse rotation to the motor driving circuit (MD) via the parallel input-output (PIO). Since the rotational angle of the interlocking arm (106) is restricted to a maximum of 40 degrees by the pair of stoppers (108a) and (108b), the arm (106) is reset to the initial position abutting the stopper (108a) irrespective of its preceding position. Even if the interlocking arm (106) abuts the stopper (108a) while the rotation of the stepping motor (SM) still remains to be completed, the subsequent rotation is absorbed by the slip mechanism. The initial applanation pressure Wi by the pickup (PU) in this state is 0.5 g. For the examination of this initial applanation pressure value Wi, the calibration element (140) illustrated in FIG. 17 is employed as explained hereinbefore.

Then, the sequence proceeds to step $ST_2$ where the microprocessor (MC) actuates the switching circuit (SC) via the parallel input-output (PIO) to set the monitor mode with video signal selected. Accordingly, the picture image on the image sensor (28) is reproduced on the CRT display (CRT).

Then, in step $ST_3$, the microprocessor (MC) judges whether the calibration signal (Cal. Sig.) outputted on closure of the calibration switch (CAL SW) was read or not. If the calibration signal (Cal. Sig.) has been read, the sequence proceeds to step $ST_4$ so that the microprocessor (MC) transmits the number of drive pulses corresponding to 2.0 g and a direction signal (DS) indicating the direction of normal rotation to the motor driving circuit (MD) via the parallel input-output means (PIO). Thus, the applanation device (PD) will generate a pressure value of 2.0 g. Then, in step $ST_5$, the microprocessor (MC) actuates the switching circuit (SC) via the parallel input-outpput (PIO) to set the character indication mode with character signal (IS) selected. In steps $ST_6$, the microprocessor (MC) transmits to the interface circuit (INT) a signal representing the pressure value 2.0 g corresponding to the number of drive pulses fed to the motor driving circuit (MD) and this signal is converted to a character signal (IS) and inputted to the CRT display (CRT), where the pressure value of 2.0 g is displayed. At this stage, the user of the device checks to see that the actual applanation pressure is 2.0 g, using the calibration element (140) of FIG. 17 as mentioned hereinbefore. Until completion of this check, the CRT display (CRT) shows the pressure value of 2.0 g in characters.

On completion of the above check of the applanation pressure value 2.0 g, the user closes the reset switch (RESET SW). In step $ST_7$, if the microprocessor (MC) reads a reset signal (Reset Sig.) outputted on closure of the reset switch (RESET SW), and the sequence returns to step $ST_1$ and the device is reset into its initial state.

If the microprocessor (M) has not read the calibration signal (Cal. Sig.) in step $ST_3$, the sequence proceeds to step $ST_8$, where the concentration and amount of fluorescein (FL) applied to the glass plate (20) of the pickup (PU) is checked as described hereinbefore. If it is judged that at least one of the concentration and amount of fluorescein (FL) is inadequate, the sequence proceeds to step $ST_9$ to switch the switching circuit (SC) to the character indication mode selecting the character signal (IS). Then, in step $ST_{10}$, it is indicated in characters that the concentration or amount of fluorescein (FL) is inadequate. This display is kept until both the concentration and amount of fluorescein have been made adequate.

On completion of this verification that the concentration and amount of fluorescein (FL) are adequate, the sequence proceeds to step $ST_{11}$, where it is judged whether the start signal (Start Sig.) generated by closure of the start switch (START SW) has been read or not. If the start signal (Start Sig.) has not been read into the microprocessor (MC), the sequence returns to step $ST_3$. In this manner, the microprocessor (MC) executes steps $ST_1$ and $ST_2$, checks the concentration and amount of fluorescein (FL) and waits for either the calibration switch (CAL.SW) or the start switch (START SW) being operated.

On reading the start signal (Start Sig.), the microprocessor (MC) proceeds to step $ST_{12}$, where it reads the initial information relating to the width of the fluorescein ring image under the initial applanation pressure value Wi(0.5 g). The sequence then proceeds to step $ST_{13}$, where the microprocessor (MC) performs the calculation based on the above initial information in accordance with the flow chart of FIG. 22 to obtain the initial area value Si corresponding to the initial applanation pressure value Wi(=0.5 g). In step $ST_{14}$, the initial intraocular pressure value Pi is calculated from the above-mentioned Wi and Si values. This calculation is performed in accordance with the formula Pi=Wi/Si. This initial intraocular pressure value Pi is not used as a measured intraocular pressure data but is used for calculating the pressure which must be applied to obtain the applanation area $S_M$ which is suitable for intraocular pressure measurement.

In step $ST_{15}$, the mircroprocessor (MC) calculates this target applanation pressure value We according to the formula We=Pi×$S_M$. Furthermore, in step $ST_{15}$, the microprocessor (MC) calculates the pressure which is obtained by multiplying the target applanation pressure value We by 0.85.

Then, the sequence proceeds to step $ST_{16}$ of FIG. 25 and the microprocessor (MC) actuates the motor driving circuit (MD) so that the applanation will progress at a high speed until the pressure to the eyeball reaches 0.85×We. This high-speed applanation is intended to reduce the time during which the eyeball is pressed by the pickup (PU) as much as possible and to thereby mitigate the discomfort of the subject whose intraocular pressure is being measured. And the above-mentioned figure of 85% of the target applanation pressure value We is based on the consideration that if the high-pressure applanation be carried out up to the target value We, the applanation area might be increased beyond the area $S_M$ suited for intraocular pressure measurement.

Then, in step $ST_{17}$, the microporcessor (MC) judges if the pressure value $W_j$ thus reached is less than the maximum applanation pressure value $W_{max}$ determined by the arrest of rotation of the interlocking arm (106) by the stopper (108b). If $W_j < W_{max}$, the sequence proceeds to $ST_{18}$ where the microprocessor (MC), via the parallel input-output (PIO), reads the width signals (WS) for respective horizontal scanning lines from the width calculation circuit (WC), i.e. the information on the detected applanation area. In step $ST_{19}$, the microprocessor (MS) calculates this area S. Then, at steps $ST_{20}$, it is judged if the calculated area S is greater than the area $S_M$ suited for intraocular pressure measurement, which is 7.35 mm².

If the calculated area S is found to be less than $S_M$ in step $ST_{20}$, the sequence proceeds to step $ST_{21}$, where the microprocessor (MC) transmits one drive pulse (DP) to the motor driving circuit (MD) via the parallel input-output (PIO). Thereafter, steps $ST_{17}$ through $ST_{21}$ area repeated until $S \geq S_M$, the area calculation being carried out while the applanation is progressively performed. If, in step $ST_{17}$, the applanation pressure value $W_j$ is found to be not less than the maximum applanation pressure value $W_{max}$, or if, in step $ST_{20}$, it is judged that $S \geq S_M$, the sequence proceeds to step $ST_{22}$ with the applanation pressure value $W_j$ in that state being held constant.

In step $ST_{22}$, with the applanation pressure value $W_j$ being held constant, the area S inside of the fluorescein ring image is calculated 32 times and the area values are respectively memorized. This calculation is completed within a period of about 1.6 seconds. This time is sufficiently longer than the adult's pulse interval of 0.9 seconds so that the changes in intraocular pressure due to the beating of the heat may be determined. However, if this time is set too long, the eyeball may move to interfere with an accurate measurement of intraocular pressure.

On completion of step $ST_{22}$, the sequence immediately proceeds to step $ST_{23}$, where the stepping motor (SM) is driven in the reverse direction to reset the applanation device to its initail state. Then, in step $ST_{24}$, the intraocular pressure value P at each time-point is calculated from the applanation pressure value $W_j$ and the 32 area values S calculated as above. Assuming that the applanation pressure value is W(g) and the 32 area values are Sj(mm²) (j=1, 2, ..., 32), the intraocular pressure values Pj(mmHg) (j=1, 2, ..., 32) can be calculated by means of the following formula.

$$Pj = \frac{760}{1033.6} \times \frac{W}{Sj} \quad (j = 1, 2, \ldots, 32)$$

Based on these 32 calculated intraocular pressure values $P_j$, the maximum intraocular pressure value $P_{max}$, minimum intraocular pressure value $P_{min}$ and mean intraocular pressure value $P_{ave}$ are calculated in step $ST_{25}$. Then, in step $ST_{26}$, the microprocessor (MC) through the parallel input-output (PIO) actuates the switching circuit (SC) to select the character indication mode in which character signals (IS) are selected. In step $ST_{27}$, the microprocessor (MC) transmits the calculated maximum, minimum and mean intraocular pressure values $P_{max}$, $P_{min}$ and $P_{ave}$ to the interface circuit (INT) so that these $P_{max}$, $P_{min}$ and $P_{ave}$ are displayed in characters on the CRT display (CRT).

Furthermore, in step $ST_{28}$, the microprocessor (MC) through said parallel input-output (PIO) transmits said $P_{max}$, $P_{min}$ and $P_{ave}$ signals to the printer (PR) which accordingly prints out the maximum, minimum and mean intraocular pressure values.

In step $ST_{29}$, the microprocessor (MC) enquires if the reset signal (Reset Sig.) generated on closure of the reset switch (RESET SW) has already been read, and if the answer is affirmative, returns to step $ST_1$. The whole device is stopped as the main switch (not shown) is opened.

Figure 24:
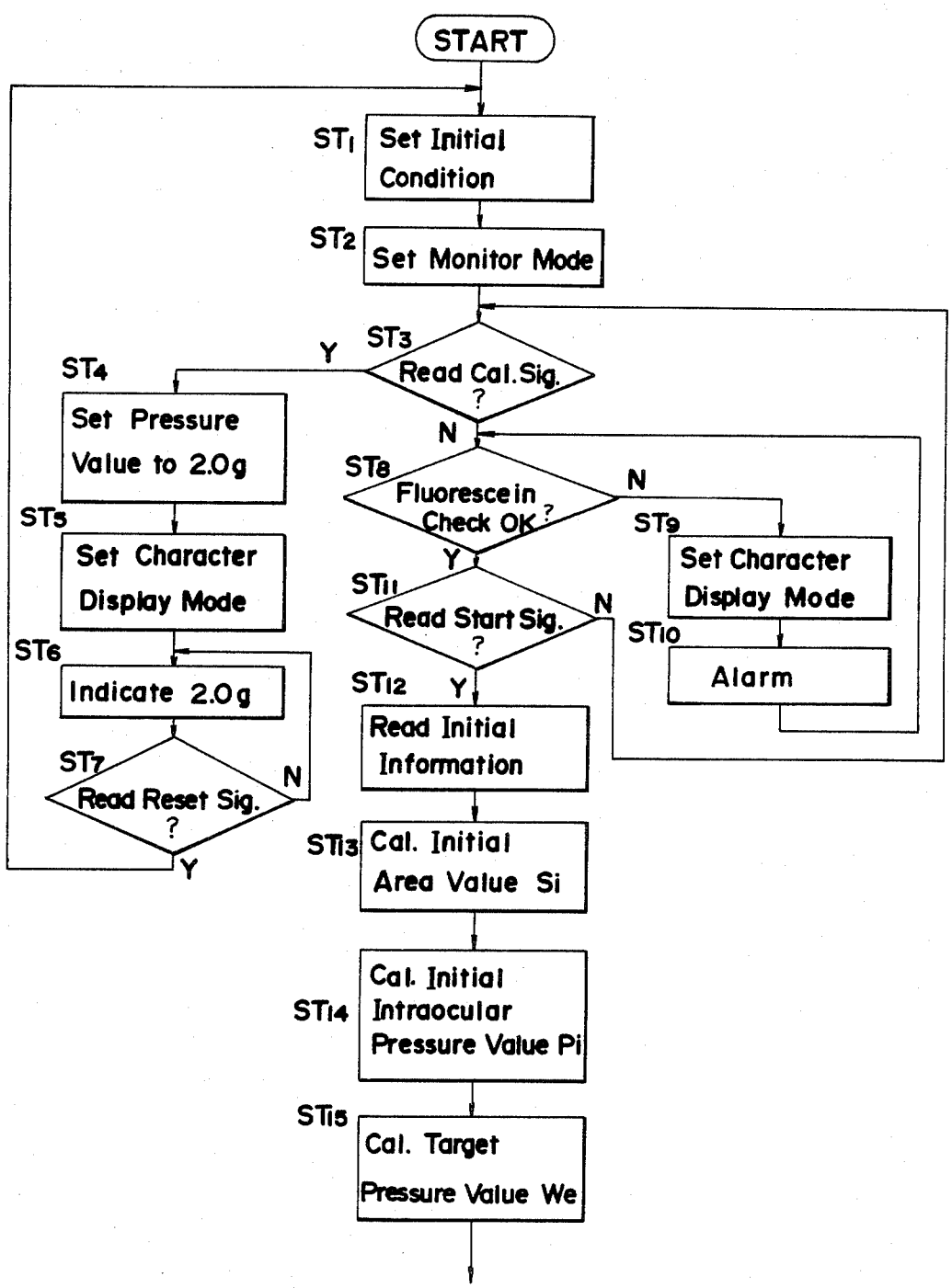
Figure 26A:
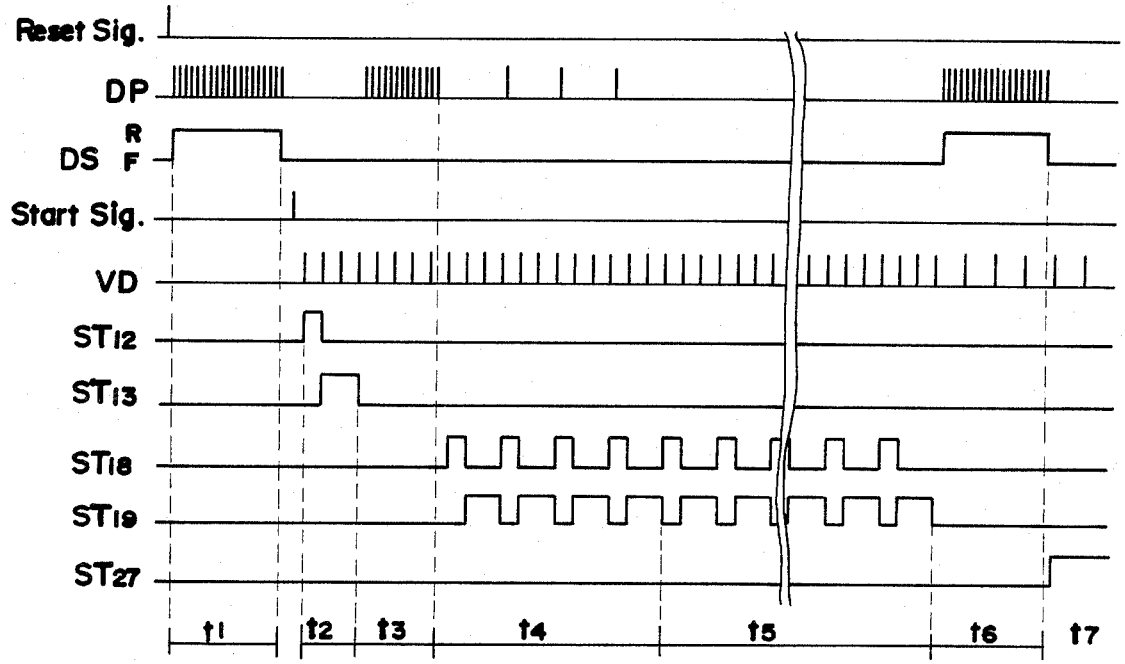
FIGS 26(a), (b) each is a timing chart showing the relationship between the generation of each signal and the execution time of each step in the embodiment.

FIG. 26(a) is a timing chart showing the output patterns of said reset signal (Reset Sig.), drive pulse (DP), direction signal (DS), start signal (Start Sig.) and vertical synchronizing signal (VD) and the operation timings of the steps $ST_{12}$, $ST_{13}$, $ST_{18}$, $ST_{19}$ and $ST_{21}$ in the flow charts of FIGS. 24 and 25. Referring to this FIG. 26(a), the section ($t_1$) is the time period during which the stepping motor (SM) is rotated counterclockwise at a high speed as will be apparent from step $ST_1$. The section ($t_2$) is the time period during which the initial area value Si corresponding to the initial applanation pressure value Wi is calculated. The section ($t_3$) is the time period during which the high-speed applanation is being carried out in accordance with the calculated target applanation pressure value We. The section ($t_4$) is the time period during which the closed loop of steps $ST_{17}$ through $ST_{21}$ is repeated, i.e. the time period during which the area calculation is being conducted while the applanation is continued. The section ($t_5$) is the time period during which the 32 area measurement are performed with a fixed applanation pressure. The section ($t_6$) is the time period during which the applanation device is being reset into the initial state. The section ($t_7$) is the time period during which the calculated values are displayed.

Figure 26B:
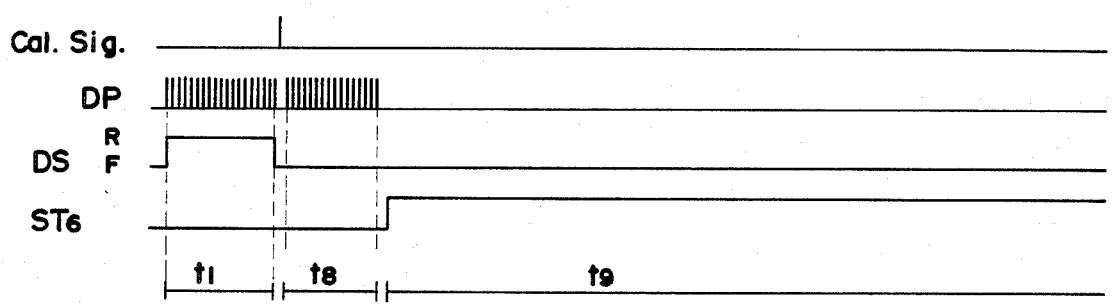

FIG. 26(b) is a timing chart showing the action which takes place when the calibration signal (Cal Sig.) has been read in step $ST_3$. The section ($t_1$) is the same time period as the corresponding time period of FIG. 26(a), the section ($t_8$) is the time period during which the applanation of 2.0 g is performed in step $ST_4$, and the section ($t_9$) is the time period during which the indication of 2.0 g is displayed.

Figure 27:
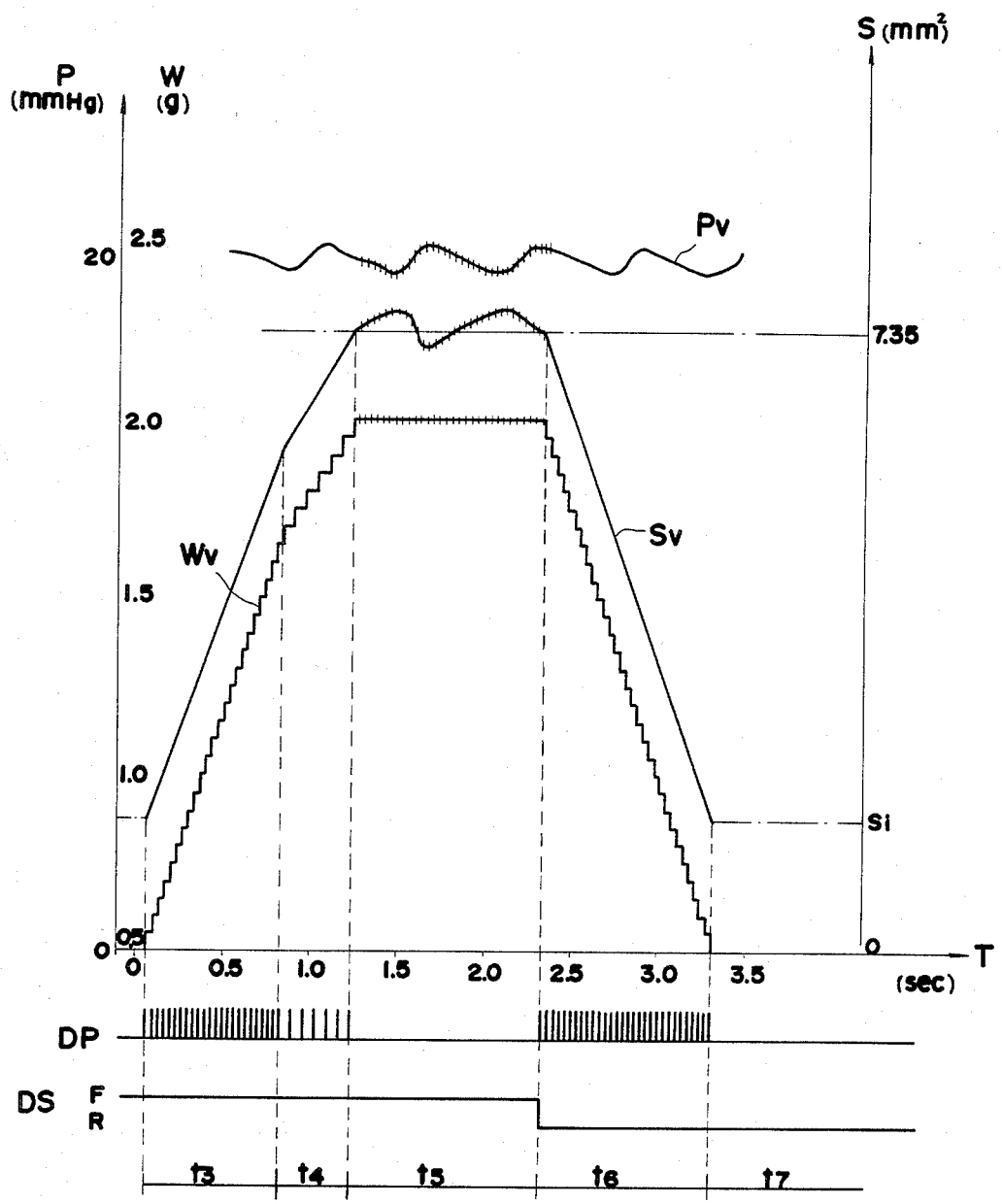
FIG. 27 is a graph showing the relationship between the time-course changes of applanation pressure, area and intraocular pressure values at intraocular pressure measurement and the signal outputting from the microprocessor to the motor driving circuit.

FIG. 27 is a series of graphs showing the changes of applanation pressure value (Wv), area value (Sv) and intraocular pressure value (Pv) during the intraocular pressure measurement of a healthy eye, together with the output patterns of drive pulse (DP) and direction signal (DS). The sections ($t_3$) through ($t_7$) correspond to those of FIG. 26(a). As will be apparent from FIG. 27, the duration of applanation of the eyeball in this embodiment may be as short as about 3.5 seconds.

Figure 28:
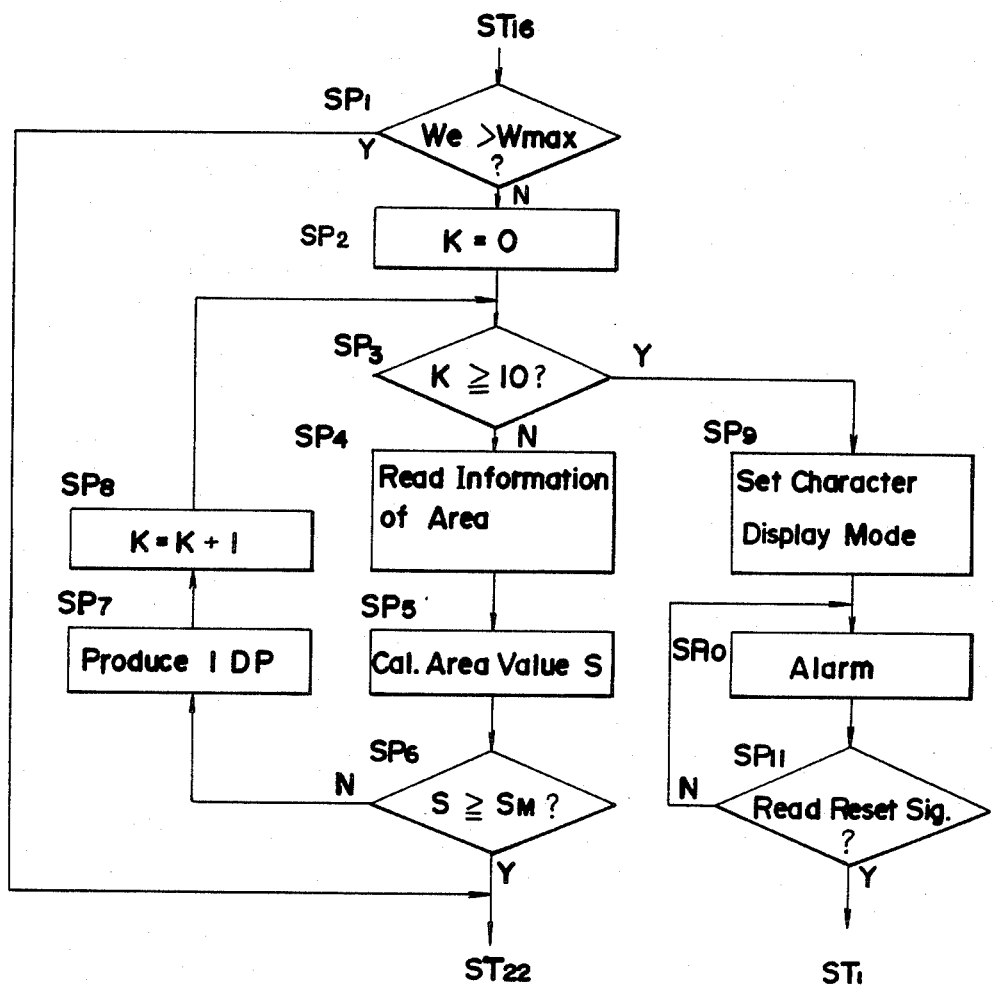
FIG. 28 is a flow chart as a modification of the flow chart shown in FIGS. 24 and 25.

FIG. 28 is a flow chart showing a modification of the steps $ST_{17}$ through $ST_{21}$ shown in FIGS. 24 and 25. In this embodiment, the microprocessor (MC) is constructed so that it can count up to 111 drive pulses (DP) as the number corresponding to the maximum applanation pressure value $W_{max}$. This is intended to prevent applanation in excess of the maximum applanation pressure value $W_{max}$ by calculation within the microprocessor (MC) and the mechanical stopper (108b) is used to prevent the pickup arm (130) from being turned to an abnormal extent by an external force on the pickup (PU) and the like or to prevent the occurrence of mechanical trouble due to the noise of drive pulses (DP). In step $ST_{16}$ of this embodiment, the number of drive pulses (DP) corresponding to the target applanation pressure value We minus 6 are transmitted to the motor driving circuit (MD) to perform the applanation. Then, in step $SP_1$, it is judged if the target applanation pressure value We is greater than the maximum applanation pressure value $W_{max}$. This judgement is made by explaining whether the number of drive pulses (DP) corresponding to the target applanation pressure value We is larger than the number 111 corresponding to the maximum applanation pressure value $W_{max}$. Then, in step $SP_2$, $K=0$ is set. The sequence further proceeds through step $SP_3$ to step $SP_4$ where the width signals (WS) required for area computation are read. In step $SP_5$, the area S is calculated. In step $SP_6$, it is examined whether the calculated area S is larger than the area $S_M$ suited for intraocular pressure measurement. If S is not larger than $S_M$, the sequence proceeds to step $SP_7$, where an additional drive pulse (DP) is outputted and the applanation is advanced. In step $SP_8$, $K=K+1$ is set. If $S \geq S_M$ in step $SP_6$, the sequence returns to the step $ST_{22}$ of FIG. 25. The sequence of steps $SP_3$ through $SP_8$ is repeated until the judgement of $S \geq S_M$ is established but if $K=10$ is detected in step $SP_3$, the sequence proceeds to step $SP_9$. Thus, the applanation corresponding to the number of drive pulses equal to the number corresponding to the target applanation pressure We minus 6 has already been made in step $ST_{16}$ and if a further 10 drive pulses be transmitted, the area $S_M$ suitable for intraocular pressure measurement would not be reached. In this condition, the switching circuit (SC) selects the character indication mode using character signals (IS) in step $SP_9$ and a warning is issued in step $SP_{10}$. As shown in step $SP_{11}$, this warning persists until the reset signal is read.

Figure 29:
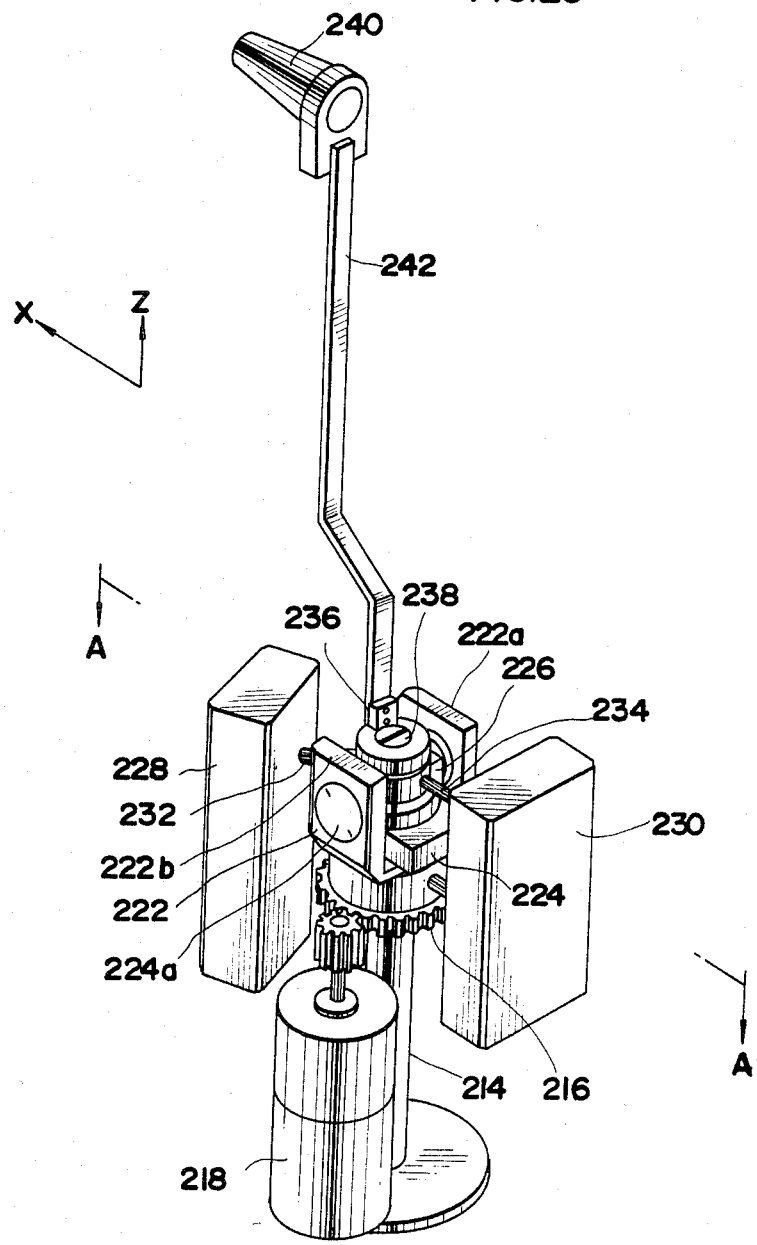
FIG. 29 is a perspective view showing an applanation device as a third embodiment of this invention.
Figure 30:
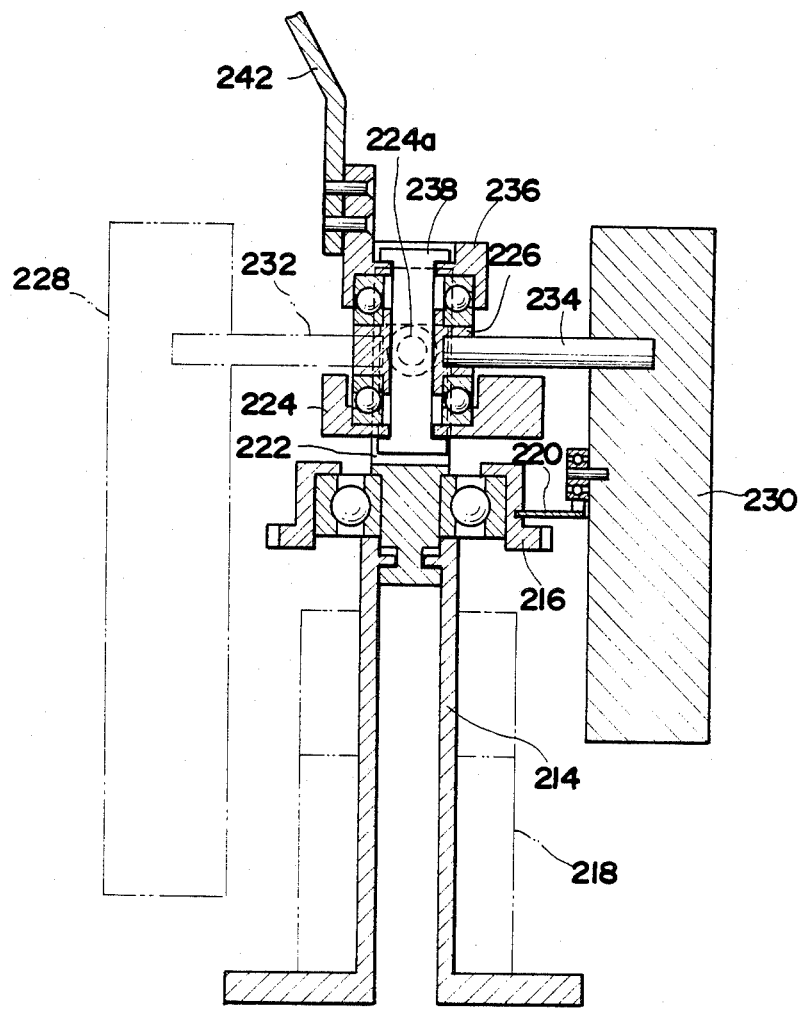
FIG. 30 is a sectional view taken along the line A—A of FIG. 29.

FIG. 29 is a perspective view showing an applanation device used in the tonometer as the third embodiment of this invention. FIG. 30 is cross-section view taken along the line A—A of FIG. 29. Referring to the figures, the reference numeral (214) indicates a post, (216) a gear rotatably mounted on said post (214), and (218) a stepping motor having a gear engaged with said gear (216). Attached to the gear (216) is an interlocking lever (220) which is engaged by a weight (230) which is to be described hereafter. As will be explained in detail, as the gear (216) is rotated by the stepping motor (218), the weight (230) is also rotated with respect to the post (214). The reference numeral (222) represents a base rigidly secured to the post (214). This base (222) has an opposed couple of flanges (222a) and (222b), which respectively have a thorough-hole. Indicated at (224) is a horizontal shaft mount which has a shaft (224a) fitting into said thorough-holes of flanges (222a) and (222b). Thus, the horizontal shaft mount (224) is swingable about this shaft (224a) with respect to the base (222).

Disposed on said horizontal shaft mount (224) is a horizontal rotary shaft (226) which is rotatably supported by an interlocking shaft (238) which is described hereinafter. Rigidly secured to this horizontal rotary shaft (226) is one end of each of weight supporting shafts (232) and (234) which carry weights (228) and (230), respectively, at the other ends thereof. The angle between the two supporting shafts (232) and (234) is fixed at about 140 degrees. Linked to said horizontal shaft mount (224) by said interlocking shaft (238) is an arm mounting base (236) which carries one end of an arm (242), the other end of which carries an applanation pickup (240) adapted to contact the eyeball. Bearings are provided between said horizontal rotary shaft (226) and horizontal shaft mount (224) and between said horizontal rotary shaft (226) and arm mounting base (236), and only the horizontal rotary (226) alone may rotate smoothly with respect to the horizontal shaft mount (224) and arm mounting base (236).

In this manner, the horizontal shaft mount (224) may rotate together with the horizontal rotary shaft (226), arm mounting base (236) and interlocking shaft (238) about the shaft (224a). Moreover, the horizontal rotary shaft (226) may rotate smoothly about the interlocking shaft (238) with respect to the horizontal shaft mount (224) and arm mounting base (236). Therefore, as the gear (216) is driven by the stepping motor (218) to turn about the post (214), its rotation is transmitted to the horizontal rotary shaft (226) through the weight (230) and weight supporting shaft (234), and the horizontal rotary shaft (226) alone is rotated about the interlocking shaft (238). By this arrangement, the rotational moment about the shaft (224a) is varied as already mentioned, with the result that the applanation pressure applied by the applanation pickup (240) to the eyeball is varied.

Figure 10C:
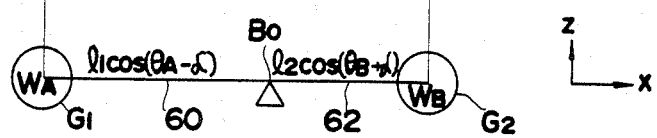

In accordance with this embodiment, the rotational moment on the xz plane is determined in accordance with the angle between the weight supporting shafts (232), (234) and the applanation direction (x-axis). And, the applanation pressure to the eyeball is calculated in accordance with the result. Therefore, the applanation pressure value can be easily calculated in accordance with the number of pulses transmitted to the stepping motor. Moreover, since the rotation of the stepping motor need not be converted to a linear motion, the construction of the device is simplified. Thus, the construction is suitable for varying the applanation pressure by means of a stepping motor. Furthermore, in accordance with this embodiment, unlike the construction in which one of the weight supporting shafts are fixed, the other weight supporting shaft is driven to vary the angle between the two shafts, it is not necessary to provide a mechanism for changing the angle between the two shafts, with the result that the construction is much simplified. Moreover, when the weight supporting arms are moved from the position indicated by dotted lines to the position indicated by solid lines as illustrated in FIG. 10(a), the distance in the X-direction between the fulcrum and the eight ($G_1$) on the left side is increase while the distance in x-direction between the fulcrum and the weight ($G_2$) on the right side is decreased as will be apparent from FIGS. 10 (b) and (c), with the result that the rotation moment in a counterclockwise direction is invariably increased. This means that the pressure acting on the eyeball can be effectively altered by a small amount of rotation. To accomplish this result, the two weights ($G_1$ and $G_2$) must be on the same side with respect to the xz plane. Moreover, the angle between the two weights must be other than 180 degrees.

Various examples of the auxiliary device used for applying a small amount of fluorescein to the center of the front surface of the applanation pickup will be described below.

Figure 31:
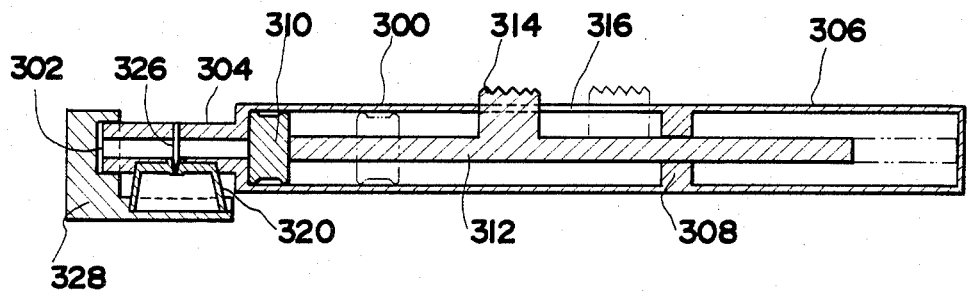
FIG. 31 is a sectional view showing the first embodiment of the auxiliary device.
Figure 32:
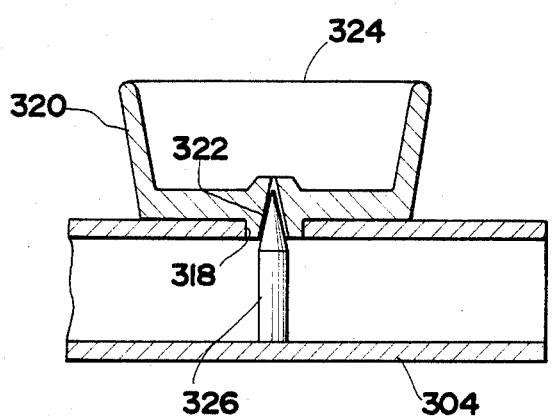
FIG. 32 is a sectional view on an exaggerated scale of an important part of the first embodiment of the auxiliary device.
Figure 33:
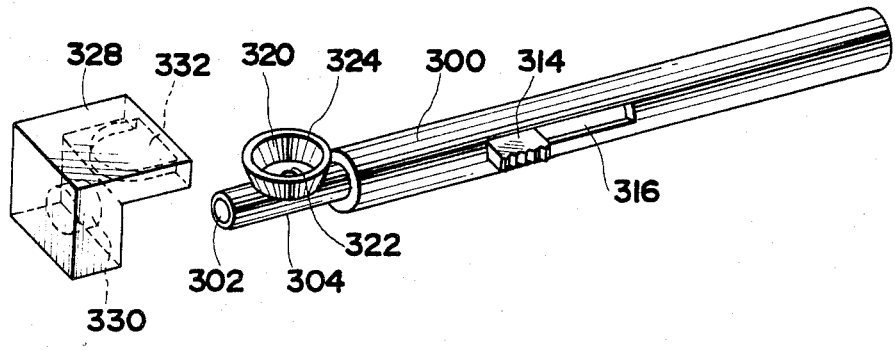
FIG. 33 is a perspective view of the first embodiment of the auxiliary device.

FIG. 31 is a longitudinal section view showing an embodiment of the auxiliary device; FIG. 32 is a longitudinal section view with an exaggerated scale of the main part of said embodiment; and FIG. 33 is a perspective view thereof. Referring to FIG. 31, an auxiliary device body (300) made of a transparent or translucent material comprises a small-diameter portion (304) having a solution feed port (302) at one end for filling a solution of fluorescent material (e.g. fluorescein) and a large-diameter portion (306). Disposed inside of the large-diameter portion (306) is a guide means (308) by which an operating member (312) carrying a rubber cylinder (310) fixed to one end thereof is guided so that is may move right and left as viewed in the figures with respect to the body (300). The operating member (312)

has an operating element (314) which is extending out through a slot (316) in the side wall of said large-diameter portion (306) extending right and left as viewed in the figure, so that it can be manipulated by hand. Therefore, by gripping the large-diameter portion (306) of the body and sliding the operating element (314) by finger, the rubber cylinder (310) can be relatively shifted with respect to the large-diameter portion (306).

As shown on an exaggerated scale in FIG. 32, a circular opening (318) is formed in a part of the side wall of said small-diameter portion (304) and a guide member (320) is rigidly secured to the part. For the purpose of applying a very small amount of fluoresein to the center of the tip surface of the applanation pickup, the guide member (320) is used to determine the relative position of the applanation pickup and the auxiliary device. The guide member (320) has a very small conical hole (322) whose diameter diminishes progressively outwardly and which communicates with the inside of the small-diameter portion (304). Furthermore, the guide member (320) has a conical guide wall (324) whose diameter increases progressively outwardly and this wall (324) has a slightly larger diameter, even at the smallest diameter portion, than the diameter of the tip surface of the applanation pickup. Therefore, when the tip of the applanation pickup is inserted into this guide member (320), it is guided by said guide wall (324) so that the approximate center of the tip surface of the applanation pickup is brought into contact with the tip end of the small hole (322), whereby the fluorescein is applied to the tip surface of the pickup.

Mounted on the inside wall of the small-diameter portion (304) in the position opposed to said small hole (322) is a guide needle (326) having a conical tip penetrating into said small hole (322). When this guide needle (326) is immersed in the fluorescein filled into the small-diameter portion (304), the fluoresein flows through a small clearance between the tip of said guide (326) and the conical hole (322) and a limited amount of the fluorescein is oozed out from the end of the small hole (322) by capillary action. The diameter of this tip of the small hole (322) is as small as about 0.2 mm.

Referring back to FIG. 31, for the purpose of preventing loss of the fluorescein from the auxiliary device while it is not in use, a protective cover (328) is provided to cover the auxiliary device body (300). As shown in the perspective view of FIG. 33, this protective cover (328) is a substantially L-shaped member comprising a feed port protective portion (330) adapted to cover the solution feed port (302) and a guide protective portion (332) adapted to cover the guide member (320). The protective cover (328) can be detached from or attached to the auxiliary device body (300) by moving it right and left as viewed in the figure with respect to the body (300).

Figure 34:
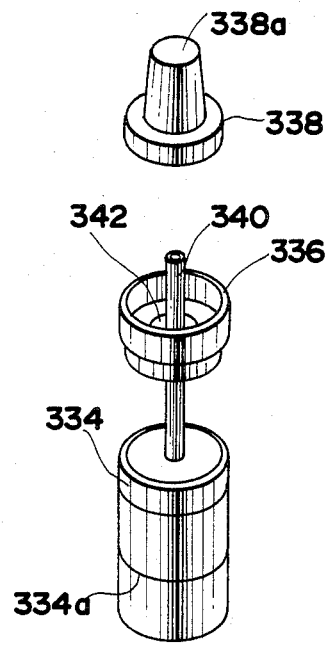
FIG. 34 is a perspective view of the embodiment of the fluorescein case.
Figure 35:
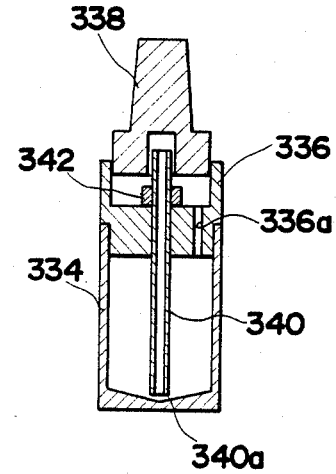
FIG. 35 is a sectional view of the fluorescein case.

FIG. 34 is a disassembled perspective view showing the solution feeding case used for filling the above auxiliary device with fluorescein, and FIG. 35 is a longitudinal section view of the same. Referring to these figures, this case comprises a container (334) adapted to contain fluorescein, an inner cover (336) and an outer cover (338). The container (334) has a graduation (334a) corresponding to 1 cc. To fill the container with fluorescein, the outer and inner covers (336, 338) are removed, then distilled water is added up to the above-mentioned graduation mark (334a), and 2 strips of fluorescein paper are put and immersed in the distilled water for a few seconds, whereby a fluorescein solution of suitable concentration can be prepared. The inner cover (336) has a pipe (340) extending therethrough in the center thereof so that a lower end (340a) of the pipe (340) may lie near to the bottom of the container (334) when the inner cover (336) has been set in position on the container (334). This inner cover (336) is further provided with an air vent hole (336a), and packing (342) disposed in concentric relation with the pipe (340). The outer cover (338) is removable with respect to the inner cover (336) and also to the container (334), and its tip (338a) has the same configuration as the tip of the application pickup. This is to ensure that the outer cap (338) can be used to examine if the fluorescein may be properly applied with the auxiliary device.

First, to fill the auxiliary device with fluorescein, the outer cover (338) is detached from the case containing the fluorescein solution prepared as above and the protective cover (328) is also detached from the auxiliary device body (300). The pipe (340) is then inserted into the solution feed port (302) of the auxiliary device body (300) until the packing (342) contacts the solution feed port (302). If, in this condition, the operating element (314) of FIG. 31 is drawn to the right as viewed in the figure, the fluorescein solution in the container (334) is sucked into the small-diameter portion (304) of the auxiliary device body (300). In the state shown by broken lines in FIG. 31 wherein one end of the operating element (314) is abutted against the closed end wall of the large-diameter portion (306), the auxiliary device body (300) is filled up with the fluorescein solution. Here, since its volume can be view through the body (300), the proper amount can be selected according to the number of subjects.

Now, the auxiliary device body (300) is held in an upright portion with the solution feed port (302) up, and the operating element (314) is manipulated again so that the fluorescein immerses the guide needle (326). Thereupon, the fluorescein solution oozes out from the small hole (322) in a limited amount by capillary action. If, in this condition, the tip of the applanation pickup is inserted into the guide member (320), a limited amount of fluorescein is applied to the approximate center of its tip surface.

Thereafter, the applanation type tonometer described hereinbefore is started and the eyeball is pressed by means of the applanation pickup. Then, the intraocular pressure can be determined from the applanation pressure value and the size of the flattened area of the eyeball as described hereinbefore. When the tip surface of the applanation pickup contacts the eyeball, the fluorescein is instilled into the eye and a fluorescein ring is formed around the flattened area. The construction and operation of the tonometer as such have been described in detail in the U.S. Pat. No. 3,070,997 referred to above and in the embodiments hereinbefore shown and described and, therefore, will not be explained again here.

In this embodiment, unless the guide needle (326) is immersed in the fluorescein solution, the capillary action does not take place and, therefore, the fluorescein does not issue out from the small hole (322). Therefore, when the volume of fluorescein filled into the device has decreased, it is necessary to manipulate the operating element (314) to bring the level of the fluorescein over the guide needle (326).

Figure 36:
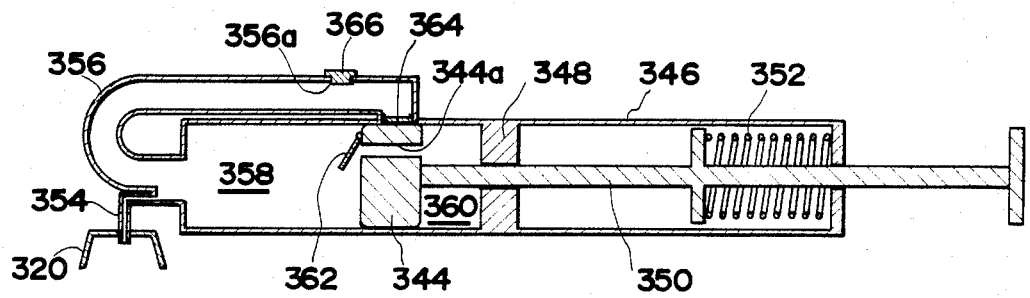
FIGS. 36, 37 each is a sectional view of the second embodiment of the auxiliary device.
Figure 37:
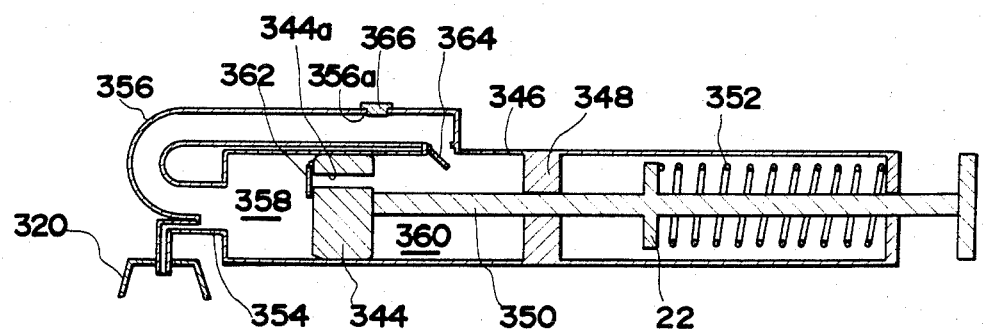

Since, in accordance with this embodiment, the instillation amount of fluorescein is determined by capillary action, savings of fluorescein can be effected substantially without incurring loses. Moreover, in this embodiment, the intraocular pressure measurement is started after inserting the tip of the applanation pickup into the guide member, the fluorescein solution is automatically instilled, so that both time and operation can be saved and the discomfort of subjects can also be mitigated. FIGS. 36 and 37 are longitudinal section views showing a further example of the auxiliary device. Referring to the two figures, piston (344) is guided by a journal (348) of a body (346) and is rigidly secured to one end of a piston rod (350) which is capable of relative movement in the right and left direction as viewed in the figures. The piston rod (350) is biased by a spring (352) toward the right-hand side in the position indicated in FIG. 36 and the other end of the piston rod (350) is exposed so that it can be manually operated. The tip of the body (346) is divided into a small-diameter conduit (354) and a large-diameter bypass conduit (356). A guide member (320) similar to that shown in FIG. 31 is rigidly secured to the tip of the small-diameter conduit (354). The space for containing the fluorescein solution is divided by the piston (344) into a first compartment (358) and a second compartment (360). The piston (344) has formed therein a through-hole (344a) communicating between the two compartments. Moreover, a check valve (362) is provided as shown for the purpose of preventing in-flow of the fluorescein from the first compartment (358) into the second compartment (36) through said through-hole (344a).

The bypass conduit (356) is provided so that most of the fluorescein in the first compartment (358) compressed by the piston (344) may be bypassed into the second compartment (360). A check valve (364) is disposed at the terminal end of the bypass conduit (356). An opening (356a) is formed in a portion of the exterior wall of the bypass conduit (356) and is normally plugged with a stopper (366). This opening (356a) is used for filling the fluorescein solution into the first and second compartments (358, 360), for example using a squirt.

When the piston rod (350) is pushed against the biasing force of the spring (352) from the position illustrated in FIG. 36, the check valve (362) is closed as shown in FIG. 37 so that the piston (344) compresses the fluorescein in the first compartment (358). Although most of this fluorescein solution passes through the bypass conduit (358) to force the check valve (364) open and returns to the second compartment (360), and only a small amount thereof passes down the small-diameter portion (354) to the center of the guide member (320). Therefore, as compared with the stroke of the piston (344), the amount of fluorescein forced out from the tip of the small-diameter conduit (354) is restricted to a very small amount so that the amount of fluorescein applied to the application pickup can be easily controlled to a defined small amount. In this embodiment, a still smaller defined amount can be forced out by increasing the ratio of the bore size of said bypass conduit (356) to that of said small-diameter conduit (354) or by providing a buffer chamber with the small-diameter chamber (354), for instance. And when it is designed that just a suitable amount will be forced out by a single full stroke of the piston rod (350), it will be necessary to control the pushing force and stroke of the piston rod (350).

As the piston rod (350) is released, it returns to the position shown in FIG. 36 by force of said spring (352). In this process, the check valve (364) closes and the check valve (364) opens so that the fluorescein in the second compartment (360) flows back into the first compartment through said through-hole (344a).

Figure 38:
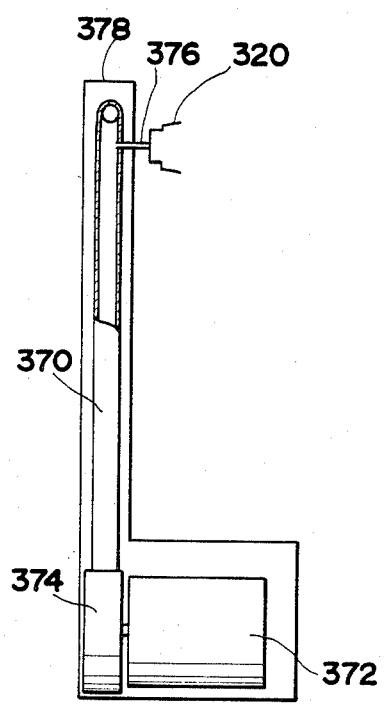
FIG. 38 is a side view of the applanation device including the third embodiment of the auxiliary device.
Figure 39:
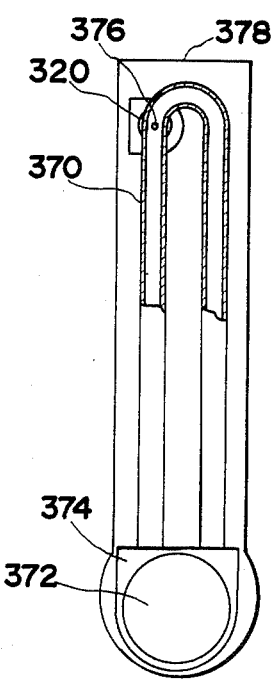
FIG. 39 is a front view of the applanation device including the third embodiment.
Figure 40:
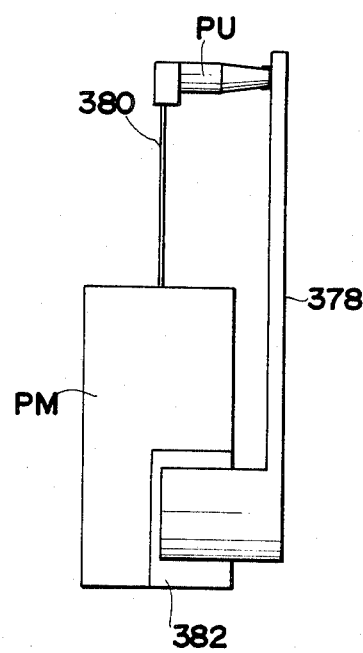
FIG. 40 is a side view when the fluorescein liquid is attached to the front surface of the pickup.
Figure 41:
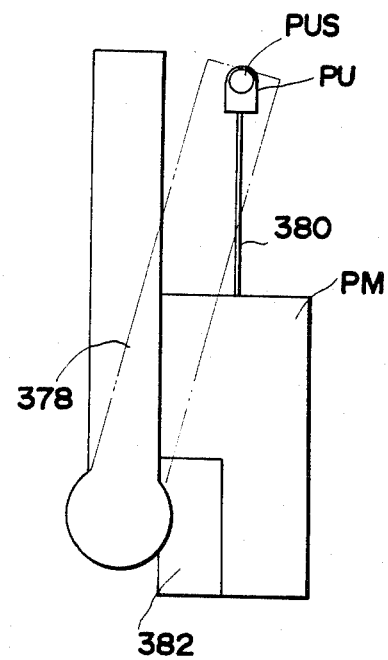
FIG. 41 is a front view when the auxiliary device is retracted from its operating position.

FIGS. 38 through 41 show a third example of the auxiliary device. FIG. 38 is a partial longitudinal side elevation view of the auxiliary device, FIG. 39 is a transverse front view of a portion thereof, FIG. 40 is side elevation view showing an applanation device including the said auxiliary device, and FIG. 41 is a front view of the same. Referring to the figures, a circulation pipe (370) has been filled with a fluorescein solution and this fluorescein solution is circulated within the pipe (370) by a pump (374) which is driven by a motor (372). In an upper portion of the circulation pipe (370), one end of a communicating pipe (376) whose other end is projecting in the center of a guide member (320) is inserted. Since the fluorescein is circulated, its hydrostatic force causes a very small amount of the fluorescein to rise at the tip of the communicating pipe (376) so that it can be applied to the center of the tip surface of the applanation pickup.

These circulation pipe (370), motor (372), pump (374) communicating pipe (376) and guide member (320) are housed as a unit in a housing (378). This housing (378) is built into an applanation device (PM) which supports the applanation pickup (PU) so as to be movable as shown in FIG. 41.

This applanation device (PM) includes a motor (382) by which the housing (378) is driven between the position indicated by line and the position indicated by the dotted line in FIG. 41. The operation of this embodiment is now explained. First, the motor (382) is driven to move the housing (378) to the position indicated by dotted line in FIG. 41 and, then, the motor (372) is driven to cause the pump (374) to circulate the fluorescein within circulation pipe (370), whereby a very small amount of fluorescein is caused to rise at the tip of the communicating pipe (376). Then, as the applanation pickup (PU) is moved in the applanation direction, its tip is inserted into the guide member (320) so that the raised portion of fluorescein is applied to the center of the pickup tip. Therefore, the applanation pickup is moved back in the direction opposite to the applanation direction and the motor (382) is driven to retract the housing (378) to the position indicated by the line in FIG. 41. Then, the applanation pickup (UP) is shifted again in the applanation direction to press the eyeball so that when the tip (PUS) of the applanation pickup (PU) contacts the eyeball, the flurescein is instilled from the pickup (PU) into the eye.

What is claimed is:

1. An apparatus for measuring the intraocular pressure of an eyeball into which fluorescent liquid has been instilled, comprising an applanation pickup having a flat applanation surface;

means for pressing the eyeball with said applanation pickup in order to flatten the front surface of the eyeball by said applanation surface, said pressing means being capable of varying the pressure against the eyeball;

means for illuminating the flattened surface of the eyeball in order to excite a fluorescent ring formed around the flattened surface;

means for forming an image of said fluorescent ring;

means for receiving said image of said fluorescent ring to produce an image signal corresponding to the shape and size of said image, said receiving means including an area image sensor capable of receiving a two-dimensional image to convert it to electrical signals;

means for detecting the pressure against the eyeball by said pressing means to produce a pressure detecting signal representative of said detected pressure;

means for measuring the area surrounded by said image, based on the electrical signals from said image sensor, to produce an area signal representative of said measured area;

means for calculating the intraocular pressure of the eyeball in accordance with said pressure detecting signal and said area signal to produce an intraocular pressure signal representative of said calculated intraocular pressure; and means for indicating the intraocular pressure in accordance with said intraocular pressure signal.

2. An apparatus as claimed in claim 1, wherein said area measuring means includes means for measuring the transverse widths of said image along a plurality of scanning lines parallel to each other to produce transverse width signals each representative of the measured transverse width, and means for adding all of said transverse width signals along a direction perpendicular to said scanning lines to calculate the area surrounded by said image.

3. An apparatus as claimed in claim 2, wherein said transverse widths measuring means includes means for comparing the electrical signals from said area image sensor with a first threshold level to detect a first transverse width along each scanning line with respect to said first threshold level, means for comparing the electrical signals from said area image sensor with a second threshold level to detect a second transverse width along each scanning line with respect to said second threshold level, and means for determining the transverse width along each scanning line in accordance with said first and second transverse widths.

4. An apparatus as claimed in claim 3, wherein said first threshold level is predetermined to be higher than the dark level of said area image sensor by a predetermined amount, and wherein said second threshold level is predetermined to be higher than the first threshold level by said predetermined amount, and wherein said transverse width determining means uses the transverse width N with respect to each scanning line according to the following equation:

$$N = 2N_1 - N_2$$

wherein, $N_1$ represents the first transverse width and $N_2$ represents the second transverse width.

5. An apparatus as claimed in claim 1, further comprising means for comparing the electrical signals from said area image sensor with a predetermined third threshold level to detect a third traverse width along each of the scanning lines with respect to said third threshold level, and means for comparing said third traverse width with a predetermined width to check an amount and concentration of fluorescent material applied to the eyeball.

6. An apparatus as claimed in claim 1, wherein said image forming means includes a first positive lens component mounted on the applanation pickup, the focal plane of the first lens element being located on the applanation surface, and a second positive lens component located so that its focal plane is disposed on a light receiving surface of the image receiving means, the optical axes of the first and second components approximately coinciding with each other.

7. An apparatus as claimed in claim 6, wherein the refractive power of said image forming means is determined so that the image is equal in shape and size to the fluorescent ring formed around the flattened surface.

8. An apparatus as claimed in claim 1, wherein said pressing means includes means for driving said applanation pickup toward its applanation to generate driving force, means for transmitting said driving force to said applanation pickup, and means for controlling the driving force generated by said driving means in accordance with said pressure detecting signal.

9. An apparatus as claimed in claim 8, wherein said transmitting means includes a base member which is shifted along a predetermined straight line toward the eyeball by said driving means, and a supporting member rotatably mounted on said base member to support said applanation pickup.

10. An apparatus as claimed in claim 9, wherein said supporting member is a supporting lever mounted rotatably in the applanation direction on said base member, said applanation pickup being fixed to one end of said supporting lever.

11. An apparatus as claimed in claim 10, wherein said pressure detecting means includes means for detecting the pressure applied to said supporting member by the reaction force of the eyeball.

12. An apparatus as claimed in claim 11, wherein said pressure detecting means includes means for detecting the force applied to another end of said supporting lever to which said applanation pickup is not fixed, the distance between said another end and the fulcrum of said supporting lever being ten times as long as the distance between said fulcrum and the one end of said supporting member to which said applanation pickup is fixed, whereby, said force detecting means detects the force which is ten times as large as the pressure against the eyeball.

13. An apparatus as claimed in claim 12, wherein said force detecting means includes means for converting the pressure against the eyeball into an electrical signal representative of said detected pressure.

14. An apparatus as claimed in claim 8 wherein said control means control said pressing means so as to stop the increase of the pressure against the eyeball if said measured area reaches to a predetermined value.

15. An apparatus as claimed in claim 14, wherein said control means controls so as to maintain the pressure against the eyeball at a constant value when said measured area reaches to 7.35 mm$^2$, and wherein said intraocular pressure calculating means multiplies the detected pressure by ten to calculate the intraocular pressure.

16. An apparatus as claimed in claim 9, wherein said control means includes means for maintaining the pressure against the eyeball to a predetermined pressure, and wherein said area measuring means includes means for measuring the area surrounded with said image a plurality of times in the condition where the pressure against the eyeball is maintained to said predetermined pressure, and wherein said intraocular pressure calculating means includes means for calculating a plurality of intraocular pressures in accordance with the areas measured a plurality of times.

17. An apparatus as claimed in claim 16, wherein said intraocular pressure calculating means calcuates the maximum and minimum intraocular pressure values among a plurality of calculated intraocular pressure values.

18. An apparatus as claimed in claim 16, wherein said intraocular pressure calculating means calculates the average intraocular pressure value of a plurality of calculated intraocular pressure values.

19. An apparatus as claimed in claim 8, wherein said transmitting means includes means for limiting the movement of said applanation pickup in its applanation direction to control the pressure against the eyeball below a predetermined maximum value, and means for interrupting the transmission of the driving force to said applanation pickup when the movement of said applanation pickup is stopped by said limiting means.

20. An apparatus as claimed in claim 19, wherein said transmitting means includes means for setting the minimum pressure against the eyeball at a predetermined pressure to maintain the initial pressure against the eyeball at said predetermined pressure.

21. An apparatus as claimed in claim 20, wherein said transmitting means includes a base, a swinging member which can swing relatively to said base in a vertical plane including the applanation direction, a rotational member mounted rotatably in a horizontal plane perpendicular to said vertical plane on said swinging member, said rotational member being capable of swinging integrally with said swinging member, and a supporting arm which is fixed to said swinging member to support said applanation pickup.

22. An apparatus as claimed in claim 21, wherein both of said limiting means and said setting means limits the rotational range of said rotational member.

23. An apparatus as claimed in claim 21, wherein said transmitting means includes at least a weight fixed to said rotational member.

24. An apparatus as claimed in claim 23, wherein said transmitting means includes a pair of weights fixed to said rotational member, the angle between the weights being less than 180 degrees, said weights being located on a common side with respect to said vertical plane.

25. An apparatus as claimed in claim 1, further comprising means for displaying the image of said fluorescent ring in accordance with said image signals.

26. An apparatus as claimed in claim 25, wherein said intraocular pressure indicating means and said image displaying means includes a common display device, and said apparatus further comprising means for switching the display on said displaying means between the intraocular pressure indication and the image display.

27. An applanation device for pressing the eyeball by an applanation pickup having a flat applanation surface to flatten the front surface of said eyeball in order to measure the intraocular pressure of said eyeball, comprising;
 a base;
 a swinging member which swings relatively to said base in a vertical plane including the applanation direction in which said applanation pickup is shifted for flattening the front surface of the eyeball, and said swinging member being supported integrally with said applanation pickup;
 a rotational member mounted rotatably in a horizontal plane perpendicular to said vertical plane on said swinging member;
 means for generating a rotational force to rotate said rotational member, and
 at least a weight fixed to said rotational member; whereby said applanation pickup is moved along the applanation direction by rotating said rotational member to change the amount of pressure exerted against the eyeball.

28. An applanation device as claimed in claim 27, wherein a pair of weights are fixed to said rotational member, the angle between the weights being less than 180 degrees, said weights being located on a common side with respect to said vertical plane.

29. An applanation device as claimed in claim 28, further comprising a steping motor for rotating said rotational member.

30. An apparatus for measuring the intraocular pressure of the eyeball into which fluorescent liquid has been instilled, comprising;
 an applanation pickup having a flat applanation surface;
 means for pressing the eyeball by said applanation pickup to flatten the front surface of the eyeball by said applanation surface;
 means for measuring the area of said flattened surface of the eyeball by detecting the area surrounded with a fluorescent ring which is formed by fluorescent material applied to the eyeball and which is formed around the flattened surface to produce an area signal representative of said measured area;
 means for detecting the pressure against the eyeball by said pressing means to produce a pressure signal representative of the detected pressure;
 means for calculating the intraocular pressure in accordance with said area signal and said pressure signal;
 means for calculating a pressure value, in accordance with said area signal in an initial condition in which the pressure against the eyeball is set at a predetermined initial pressure and with said predetermined initial pressure, to produce a calculated pressure signal representative of a calculated pressure value, said calculated pressure value being slightly less than a target pressure which is calculated to be necessary in order that the area of the flattened surface reaches a predetermined proper value for measuring the intraocular pressure, and
 means for controlling the pressure against the eyeball by said pressing means in accordance with said area signal, said pressure signal, and said calculated pressure signal, so that the pressure is quickly increased until it reaches said pressure value, and that the pressure is gradually increased with the area measurement, and that the increase of the pressure is stopped when the area reaches said predetermined proper value.

31. An apparatus as claimed in claim 30, further comprising means for initially setting the applanation pickup to a predetermined position in order to set the initial pressure to said predetermined inital pressure.

32. An apparatus as claimed in claim 30, wherein said area measuring means includes means for forming an image of said fluorescent ring, and an area image sensor for receiving said image to convert the shape and size of the image into the electrical signal representative of said image.

33. An apparatus as claimed in claim 32, wherein said area measuring means includes means for detecting a transverse width of the image along each of the scanning lines of the area image sensor, said scanning lines being parallel to each other, and means for adding all of the transverse widths along the direction perpendicular to said scanning lines.

34. An apparatus as claimed in claim 30, wherein said pressure value calculating means multiplies said target pressure by a predetermined rate to obtain said pressure value.

35. An apparatus as claimed in claim 30, wherein said pressure value calculating means subtracts a predetermined amount from the target pressure to obtain said pressure value.

36. An apparatus as claimed in claim 30, wherein said pressure value calculating means includes means for calculating the initial intraocular pressure in said initial condition according to the area signal in the initial condition and said predetermined initial pressure, and means for calculating said target pressure in accordance with said initial intraocular pressure and said predetermined proper value of the area.

37. An apparatus as claimed in claim 30, wherein said control means controls said pressing means so as to interrupt the increase of the pressure when the pressure reaches to a predetermined maximum pressure.

38. An apparatus as claimed in claim 30, wherein said control means controls said pressing means so as to interrupt the increase of the pressure when the pressure is increased from said pressure value by a predetermined amount.

39. An apparatus as claimed in claim 30, wherein said intraocular pressure calculating means, said pressure value calculating means and said control means are included in a common microprocessor.

* * * * *